(12) United States Patent
Kotlikoff et al.

(10) Patent No.: US 8,445,655 B2
(45) Date of Patent: May 21, 2013

(54) FUNCTIONAL NUCLEIC ACID LIGANDS TO FLUORESCENT PROTEINS

(75) Inventors: Michael Kotlikoff, Ithaca, NY (US); John T. Lis, Ithaca, NY (US); Bo Shui, Ithaca, NY (US); Hua Shi, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 12/305,102

(22) PCT Filed: Jun. 18, 2007

(86) PCT No.: PCT/US2007/071470
§ 371 (c)(1),
(2), (4) Date: Dec. 16, 2008

(87) PCT Pub. No.: WO2007/147159
PCT Pub. Date: Dec. 21, 2007

(65) Prior Publication Data
US 2009/0197271 A1    Aug. 6, 2009

Related U.S. Application Data

(60) Provisional application No. 60/804,982, filed on Jun. 16, 2006.

(51) Int. Cl.
*C07H 21/02* (2006.01)
*C12N 15/00* (2006.01)
*C12Q 1/68* (2006.01)
*C07H 21/04* (2006.01)

(52) U.S. Cl.
USPC ........... 536/23.1; 536/24.5; 435/6.1; 435/455

(58) Field of Classification Search
None
See application file for complete search history.

(56) References Cited

U.S. PATENT DOCUMENTS

| 6,458,559 | B1 | 10/2002 | Shi et al. |
|---|---|---|---|
| 7,435,542 | B2 | 10/2008 | Shi et al. |
| 2003/0175730 | A1 | 9/2003 | Shi et al. |
| 2003/0211516 | A1 | 11/2003 | David |
| 2004/0053310 | A1 | 3/2004 | Shi et al. |
| 2005/0282190 | A1 | 12/2005 | Shi et al. |
| 2006/0088864 | A1 | 4/2006 | Smolke et al. |
| 2006/0148746 | A1 | 7/2006 | Niu et al. |
| 2008/0254446 | A1 | 10/2008 | Sode et al. |

FOREIGN PATENT DOCUMENTS

| WO | 2005049826 A1 | 6/2005 |
|---|---|---|
| WO | 2007032359 A1 | 3/2007 |

OTHER PUBLICATIONS

Grate et al., Laser-mediated, site-specific inactivation of RNA transcripts, 1999, PNAS, vol. 96, pp. 6131-6136.*
Stojanovic et al., Modular aptameric sensors, 2004, JACS, vol. 126, pp. 9266-9270.*
Bayer et al. Programmable ligand-controlled riboregulators of eukaryotic gene expression, 2005, Nature Biotechnology, vol. 23, pp. 337-343.*
Stanlis et al. "Single-strand DNA Aptamer as Probes for Protein Localization in Cells," The Journal of Histochemistry & Cytochemistry 51(1):797-808 (2003).
Seuss et al., "Conditional Gene Expression by Controlling Translation with Tetracycline-binding aptamers," Nucleic Acids Research 31(7):1853-1858 (2003).

* cited by examiner

*Primary Examiner* — Dana Shin
(74) *Attorney, Agent, or Firm* — LeClairRyan, a Professional Corporation

(57) ABSTRACT

The present invention relates to a nucleic acid aptamer having a first domain that binds to a fluorescent protein. The nucleic acid aptamer forms a molecular complex whereby the aptamer binds a fluorescent protein at the first domain. A constructed DNA molecule, expression systems, and host cells containing the molecular complex are also disclosed. The invention also relates to a system containing a first DNA molecule encoding the nucleic acid aptamer of the present invention and a second DNA molecule encoding a fluorescent protein capable of being bound by the first domain. Methods of detecting a molecular target and determining location of a molecular target using the nucleic acid aptamer of the invention are also disclosed.

21 Claims, 11 Drawing Sheets

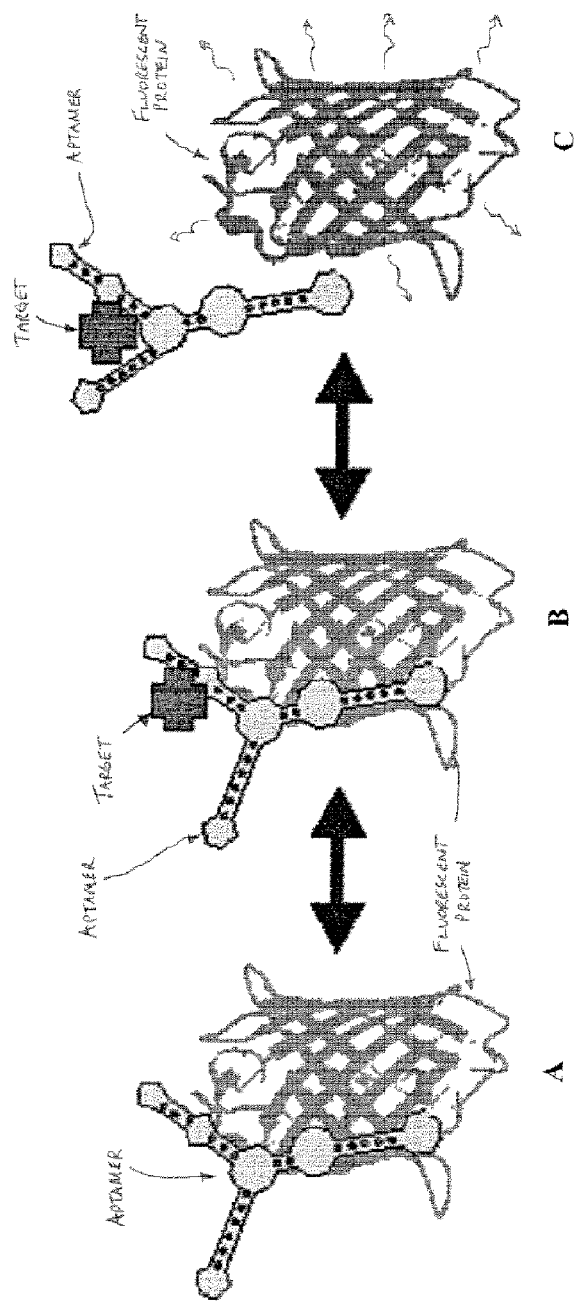
Figures 1A-C

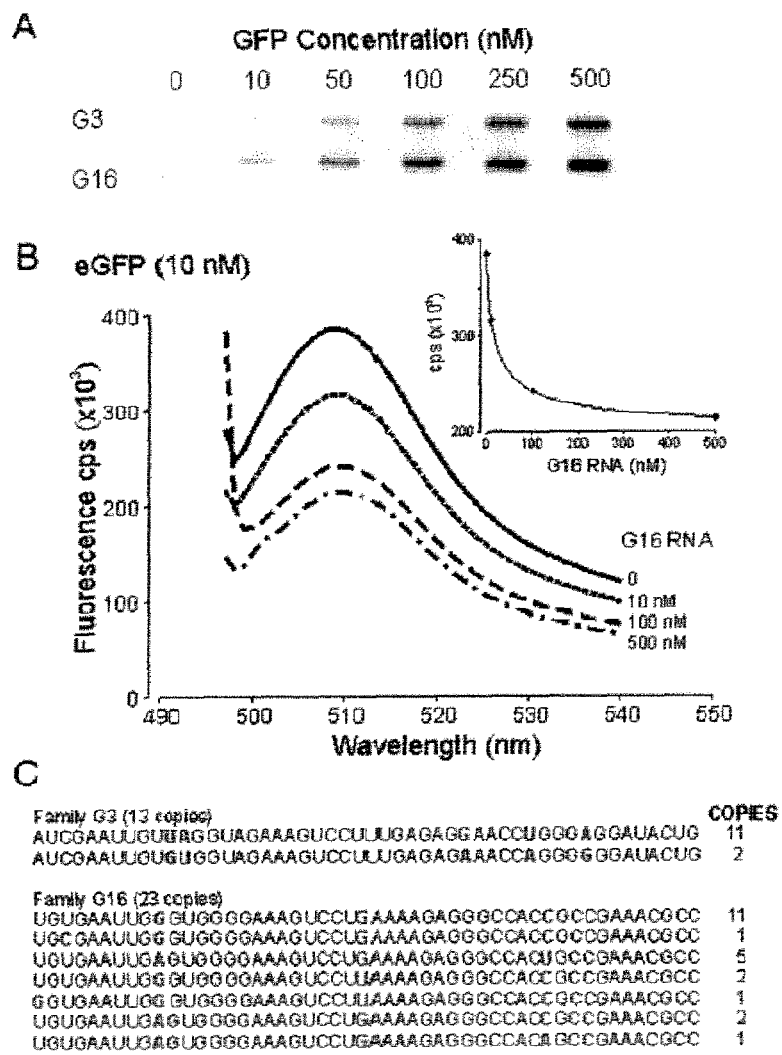
Figures 2A-C

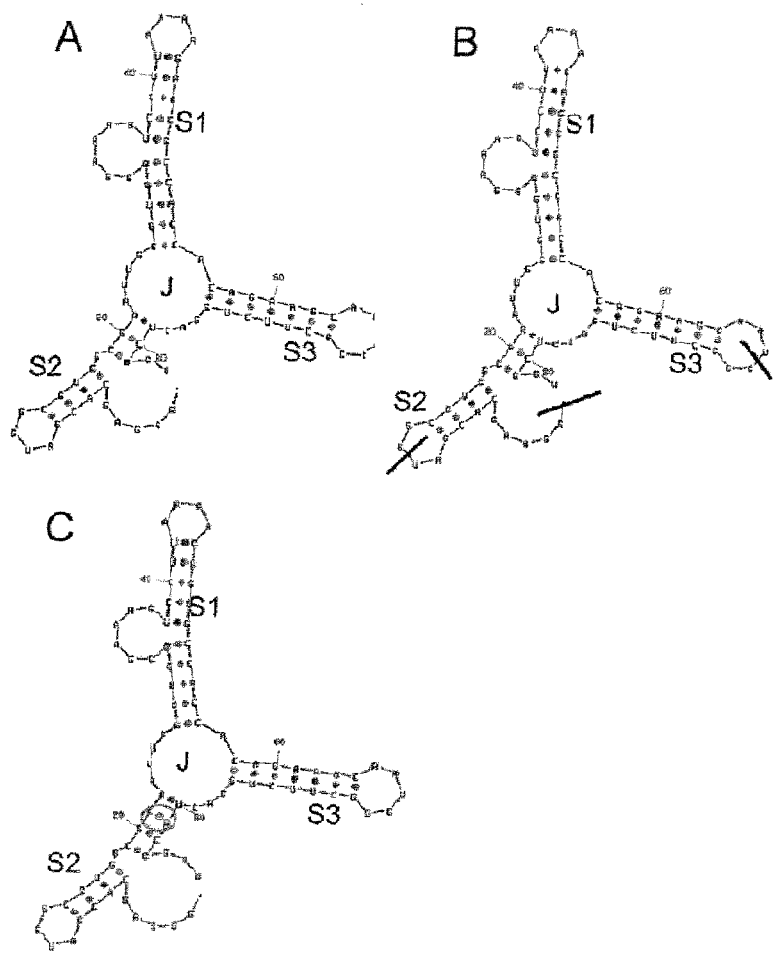
Figures 3A-C

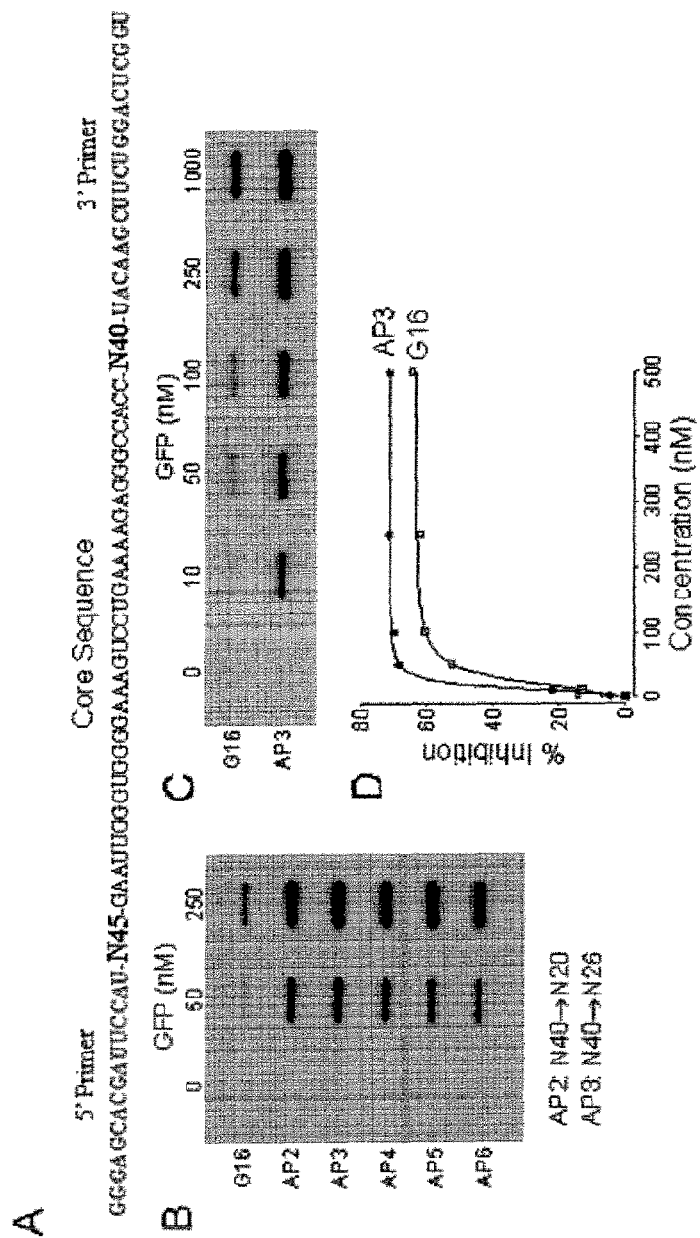
Figures 4A-D

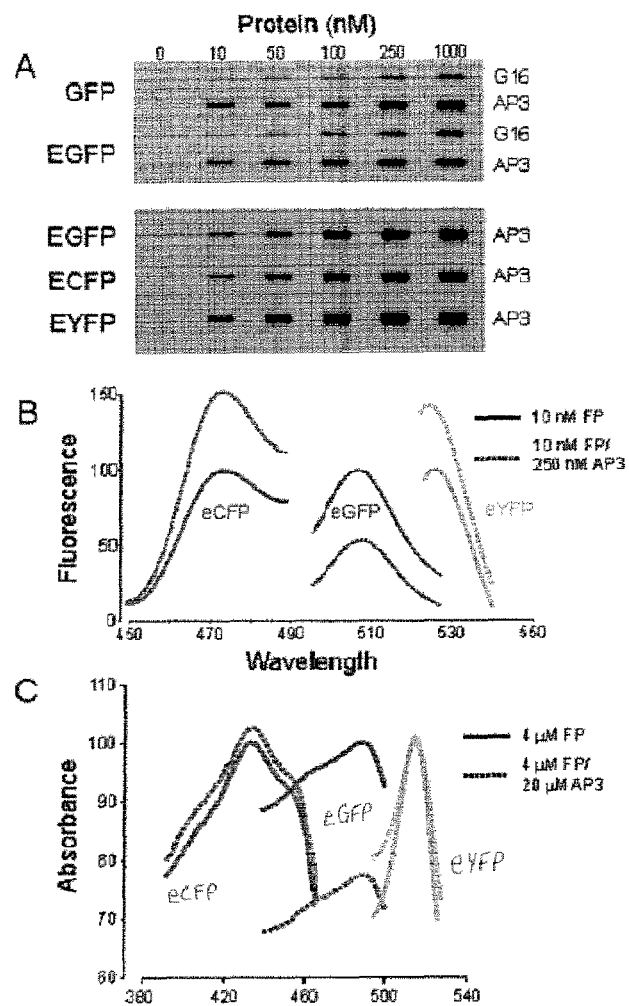
Figures 5A-C

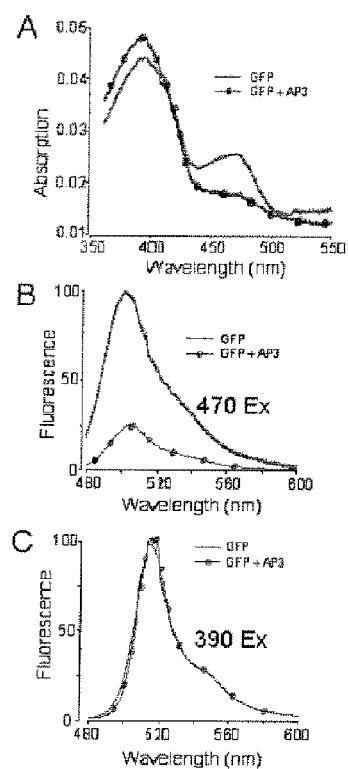
Figures 6A-C

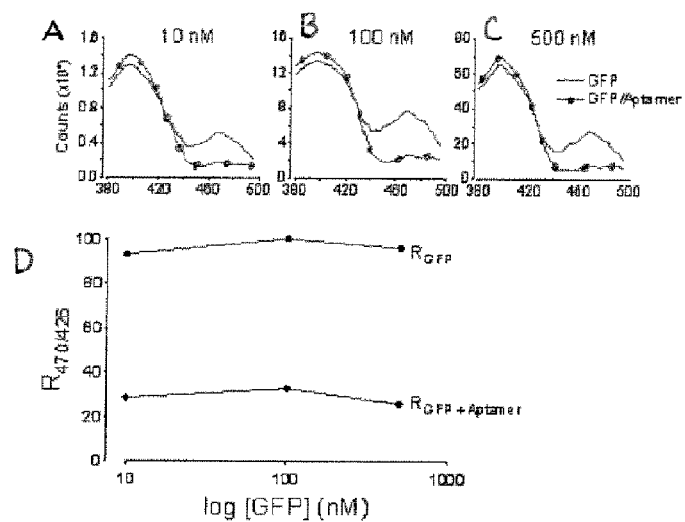
Figures 7A-D

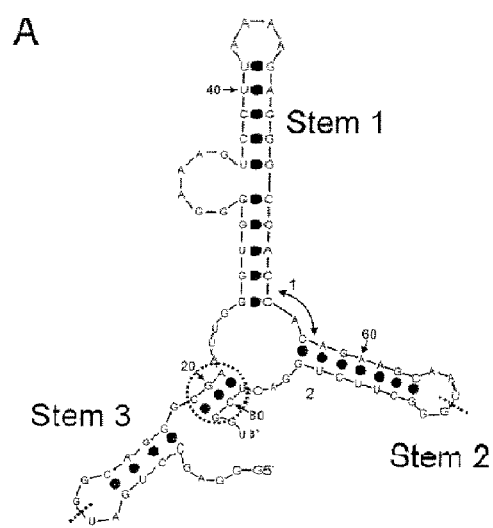
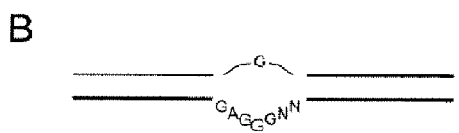
Figures 8A-B

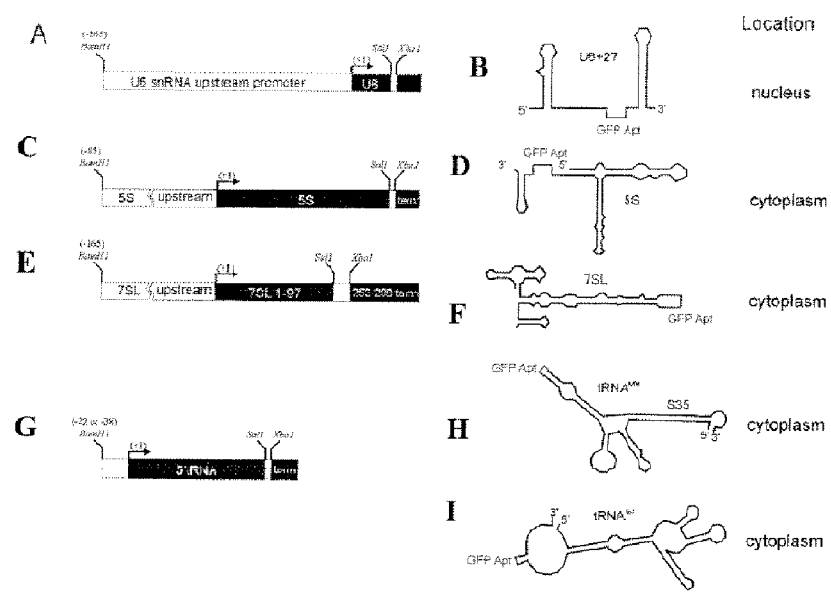
Figures 9A-I

FUNCTIONAL NUCLEIC ACID LIGANDS TO FLUORESCENT PROTEINS

This application is a national stage application under 35 U.S.C. 371 from PCT Application No. PCT/US2007/071470, filed Jun. 18, 2007, which claims the priority benefit of U.S. Provisional Patent Application Ser. No. 60/804,982, filed Jun. 16, 2006, which is hereby incorporated by reference in its entirety.

FIELD OF THE INVENTION

This invention relates to nucleic acid aptamers that bind fluorescent proteins, aptamer-fluorescent protein complexes, their expression, and methods of use.

BACKGROUND OF THE INVENTION

In the environments of living systems, protein functions are actuated through interaction with other molecules. These interactions, stable or transient, between a protein and another protein or non-protein molecule, enhance or inhibit the stability or function of one, the other, or both partners involved in the interaction. When the interaction results in a stable complex, the complex's association to yet other proteins or non-protein molecules, or a supramolecular assembly, will be affected. When a protein functions as a reagent, its specific interaction with ligands is often exploited to maximize its utility. A case in point is the fortuitous recognition of the mammalian antibody immunoglobulin G ("IgG") by the bacterial cell wall proteins streptococcal protein G and *Staphylococcus aureus* protein A.

Genetically encoded sensors that have tightly controlled and subcellularly localized expression have been constructed from polypeptides to exploit the binding characteristics of specific peptide domains (detector) to alter protein fluorescence (reporter) either directly or through resonance energy transfer, requiring a known binding partner of appropriate affinity and specificity. However, in many cases such a detector motif is not known. Examples of this difficulty include the detection of specific phosphoproteins, for which hundreds of variants may exist, and the detection of aberrantly-folded proteins, for which no known binding partners exist.

Green Fluorescent Protein ("GFP") is a natural fluorescing protein produced by the jellyfish *Aequorea victoria*. Some amino acid residues in the native protein spontaneously form a fluorophore when the polypeptide is folded into an 11-strand beta-barrel threaded by an alpha-helix running up the axis of the internal cylinder. Because it tolerates N- and C-terminal fusion to a broad variety of proteins, GFP has been used primarily as a fluorescent protein tag, i.e., for making chimeric proteins of GFP linked to other proteins where it functions as an indicator to reveal when, where, and how much of the protein it fuses to is present. In this capacity, it has been expressed in bacteria, yeast, slime mold, plants, *Drosophila*, zebrafish, and in mammalian cells.

In the jellyfish from which it was isolated, GFP is involved in physiological interactions with the bioluminescent protein aequorin and shifts its blue light absorption to green light emission through energy transfer. In most applications of GFP, this dual-component configuration is not recapitulated, and the excitation of GFP or its derivatives is afforded through optical instrumentation. Other than aequorin, one type of molecule that binds directly to GFP and its derivatives has been developed. These are antibodies, both polyclonal and monoclonal, which are usually used for signal amplification purposes when the GFP signal is too weak, or the protein has been denatured and is no longer fluorescent. In the methods utilizing these antibodies, GFP and its derivatives are treated as generic protein tags, and as such the invention of GFP antibodies and the utility thereof resides within the scope of conventional immuno-chemistry.

The prior art in the GFP related biotechnology has mainly focused on modification of the wild type GFP to increase the intensity of its fluorescence, change the wavelength of its fluorescence, and make its fluorescence conditional. General approaches to achieving these goals include (i) point mutations that change the physical-chemical environment in the vicinity of the fluorophore and (ii) topological rearrangement of the polypeptide chain that results in circular permutated or bipartite versions of the protein. These efforts have yielded many GFP derivatives that, as noninvasive fluorescent markers in living cells, allow for a wide range of applications where it may function as a cell lineage tracer, reporter of gene expression, or as a measure of protein-protein interactions.

It is desirable to find or create ligands that specifically recognize GFP and other fluorescent proteins. It is further desirable that these fluorescent protein-specific ligands can be rationally connected to ligands of other protein or non-protein molecules so that the FP-ligand complex can be recognized by other molecules, indicating the presence or absence of these other molecules.

The present invention is directed to overcoming these and other limitations in fluorescent protein technology.

SUMMARY OF THE INVENTION

A first aspect of the present invention relates to a nucleic acid aptamer having a first domain that binds to a fluorescent protein.

A second aspect of the present invention relates to a molecular complex containing the nucleic acid aptamer according to the first aspect of the present invention, with the nucleic acid aptamer bound to a fluorescent protein at the first domain. A host cell containing the molecular complex is also described.

A third aspect of the present invention relates to a method of detecting a molecular target. This method involves providing a molecular complex according to the second aspect of the present invention and contacting a molecular target with the molecular complex under conditions effective to cause a change in fluorescence of the fluorescent protein, whereby the change in fluorescence detects presence of the molecular target.

A fourth aspect of the present invention relates to a method of determining location of a molecular target. This method involves providing a molecular complex according to the second aspect of the present invention. A molecular target is contacted with the molecular complex and the fluorescence of the fluorescent protein is detected, whereby location of the molecular target is determined.

A fifth aspect of the present invention relates to a constructed DNA molecule containing a first region encoding a nucleic acid aptamer having a first domain and a second region encoding a fluorescent protein capable of binding the nucleic acid aptamer at the first domain. Expression systems and host cells containing the constructed DNA molecule are also described.

A sixth aspect of the present invention relates to a system containing a first DNA molecule encoding a nucleic acid aptamer according to the first aspect of the present invention and a second DNA molecule encoding a fluorescent protein capable of being bound by the nucleic acid aptamer at the first domain thereof. Expression systems and host cells containing the system are also described.

The present invention is directed to novel nucleic acid ligands to fluorescent proteins and their derivatives that are capable of (i) modulating the fluorescence of the protein and (ii) being connected arbitrarily to ligands directed to other protein or non-protein molecules. According to some embodiments, nucleic acid aptamers of the present invention operate as relatively simple fluorescent switches. The affinity of nucleic acid aptamers to fluorescent proteins will be regulated by the binding of a molecule to be detected. This binding will perturb the highly specific structural interaction between the aptamer and fluorescent protein, thereby resulting in unbinding and a fluorescent signal proportional to the concentration of the analyte. The present invention also provides a flexible, genetically encoded, real time detector system. Given the extreme size and diversity of the aptamer structural space, this strategy may be applied to sensors for virtually any defined target.

Distinctive from previous approaches to modifying GFP per se, the present invention enables the integration of any fluorescent protein and its derivatives into any natural or synthetic molecular network. As a result, the utility of fluorescent proteins and their derivatives are extended from passively reporting the presence of a protein to which the fluorescent protein is covalently fused, to actively functioning as a component of molecular control devices or as a method of detecting the presence of other molecules that are not covalently linked to the fluorescent protein.

The present invention provides several advantages to other methods of detecting the presence of and/or determining the location of target molecules. The methods are rapid and do not require special processing for detection, but can be simply analyzed by optical detection of fluorescence. The molecular complexes and systems for carrying out the methods of the invention can be entirely genetically encoded, providing for generalized detection of biomarkers in cells and animals. In addition, the systems take advantage of many existing cells and tissues that have been genetically engineered to express fluorescent proteins in specific contexts. The methods can be carried out in simple organisms such as bacteria or yeast, which can act as living biodetectors of accumulated exposure to biohazards, through the progressive accumulation or metabolism of substances. In carrying out the methods of the invention, multiple signals could be simultaneously detected through the use of discreet sensing aptamers with affinity for specific fluorescent proteins and target molecules.

The present invention affords the construction of a cellular imaging system based on RNA aptamers that functionally interact with fluorescent proteins. As hundreds of lines of mice expressing variants of GFP in a tissue-specific, subcellularly localized, or temporally controlled manner currently exist, such a system can immediately be used to examine cell signaling in various experimental contexts by crossing these mice with RNA aptamer-expressing lines. Ideally, these systems can be flexibly adapted to the detection of a wide range of molecules, which would have high signal characteristics, and would allow dynamic monitoring of molecular interactions in vivo. Moreover, aptamers with specificity for other fluorescent proteins can be developed, providing the potential of monitoring multiple cellular signals simultaneously.

BRIEF DESCRIPTION OF THE DRAWINGS

FIGS. 1A-C illustrate one embodiment of an aptamer/fluorescent protein signaling system of the present invention.

In FIG. 1A, a bivalent aptamer bound to a fluorescent protein markedly reduces fluorescence of the fluorescent protein. Binding of a target molecule (FIG. 1B) leads to an alteration in the tertiary structure of the aptamer, resulting in unbinding from the fluorescent protein and recovery of fluorescence (FIG. 1C).

FIGS. 2A-C demonstrate the structure and function of one embodiment of nucleic acid aptamers of the present invention. FIG. 2A is an image showing binding of representatives of two selected aptamer families to GFP on a nitrocellulose membrane. FIG. 2B is an emission spectrum for eGFP (excited at 488 nm) in the presence of an increasing concentration of aptamer G16. The inset graph of FIG. 2B shows fit of fluorescence at 510 nm to a Hill plot. The nucleic acid aptamers themselves had no measurable fluorescence. FIG. 2C shows sequence results (from top to bottom: SEQ ID NO: 2, SEQ ID NO:3, SEQ ID NO:5, SEQ ID NO:6, SEQ ID NO:7, SEQ ID NO:8, SEQ ID NO:9, SEQ ID NO:10, and SEQ ID NO: 11) from 15 rounds of SELEX. The first sequence in each family was amplified for the experiments shown in FIGS. 2A-B.

FIGS. 3A-C are illustrations of the predicted secondary structure of nucleic acid aptamers described in FIG. 2C. As shown, the structures have a three-way junction (J) that connects two stems (S1, S2) and a third stem (S3) with an apical loop and an internal loop or bulge. FIGS. 3A-C are the predicted structure of the aptamers (e.g., SEQ ID NO:29) having any of the core sequences identified in FIG. 2C, which demonstrates the ability to make conservative substitutions in the core sequence without altering the secondary structure of the nucleic acid aptamer. As illustrated in FIG. 3B, activity can be preserved with permutations of the core sequence at the indicated sites. As shown in FIG. 3C, substitutions within the iterated sequences also conserve this secondary structure.

FIGS. 4A-D show the second round design of nucleic acid aptamers according to one embodiment of the present invention. A general sequence of the aptamer is identified in FIG. 4A (SEQ ID NO:33). "N45" and "N40" represent random nucleotides flanking the core sequence identified in the first SELEX (i.e., the sequences shown in FIG. 2C). FIG. 4B is an image showing GFP binding of individual clones from the second SELEX (AP2-AP6). A markedly higher binding affinity was achieved relative to G16 (first SELEX). The random N40 sequences of AP2 and AP3 were shortened to random N20 and N26 sequences, respectively. FIG. 4C is an image comparing (shortened) AP3 and G16 binding to FGP on nitrocellulose membrane. FIG. 4D is a graph of the fluorescence inhibition caused by G16 and AP3, showing the higher affinity and greater maximum effect of AP3. GFP concentration was 10 nM.

FIGS. 5A-C show the specificity of nucleic acid aptamers of the present invention. FIG. 5A is an image demonstrating binding of two aptamer families to GFP and eGFP, showing similar affinities to both proteins, but markedly high binding affinity of AP3. Binding is roughly equivalent to all of the fluorescent proteins. In FIG. 5B, fluorescence emission scans of enhanced fluorescence proteins show the effect of AP3 aptamer. All spectra are normalized to peak fluorescence in the absence of aptamer. An increase in eCFP and eYFP fluorescence is noted in the presence of aptamer. FIG. 5C is a graph showing that AP3 decreases absorbance of eGFP at excitation peaks, whereas eCFP and eYFP fluorescence is slightly increased.

FIGS. 6A-C are graphs showing the effect of AP3 on GFP fluorescence. Spectra show effect of AP3 on GFP absorbance (FIG. 6A) and emission with 470 nm (FIG. 6B) and 390 nm (FIG. 6C) excitation. There is a marked decrease in absorption at 470 nm, with a quantitatively smaller increase in absorption at 390 nm. Emission is reduced by approximately 75% at 470 nm excitation, but increased slightly when excited at the lower absorption peak. FIGS. 6A-C are normalized to GFP fluorescence.

FIGS. 7A-D are graphs showing aptamer binding to GFP. FIGS. 7A-C show emission spectra for GFP and GFP/aptamer (1 μM aptamer) at varied concentrations of GFP, including 10 nm (FIG. 7A), 100 nm (FIG. 7B), and 500 nm (FIG. 7C). The graph in FIG. 7D demonstrates that the 470/426 fluorescence ratio is insensitive to the GFP concentration. Note that the fractional change in the ratio with aptamer binding is stable (varies less than 3%) and displays a dynamic range of approximately 3.

FIGS. 8A-B are illustrations showing the structure of GFP aptamers. FIG. 8A is the confirmed structure of a GFP aptamer (SEQ ID NO:30), where the dotted lines show other fully functional 5'/3' sites. The dotted circle on stem 3 indicates an example of a site in which addition of a pair of nucleotides at position 21 and 79 does not alter function, whereas unpairing circled nucleotides resulted in loss of function. Extension of angle between Stem 1 and Stem 2 by insertion of nucleotides (arrow 1) also degraded function. FIG. 8B illustrates that reoptimization of Stem 3 resulted in reduction to only molecules containing the critical midstem loop. Removal of nucleotides within this loop, even in the open form shown in FIG. 8A, resulted in loss of function.

FIGS. 9A-I illustrate chimeric RNA expression vectors to be tested for direction of nuclear and cytoplasmic expression of FQAs. FIGS. 9A-B illustrate the Pol III vector which is commonly used for siRNA expression. Without nuclear export signals, little aptamer is expected to be transported to the cytoplasm. FIGS. 9C-I are illustrations of chimeric constructs designed to mimic ribosomal (FIGS. 9C-F) or tRNA (FIGS. 9G-I) processing. In FIGS. 9A, 9C, 9E, and 9G, the black boxes denote structural RNA sequence from sn, ribosomal, or tRNA. The GFP aptamer will be inserted at the Sal1/Xba1 site in all constructs. FIGS. 9B, 9D, 9F, 9H, and 9I illustrate the chimeric RNA with the GFP aptamer location indicated by the partial box identified as "GFP Apt." The fluorescence quenching aptamer is encoded beginning with the end of stem 2 (FIG. 8A).

DETAILED DESCRIPTION OF THE INVENTION

Figure 10:
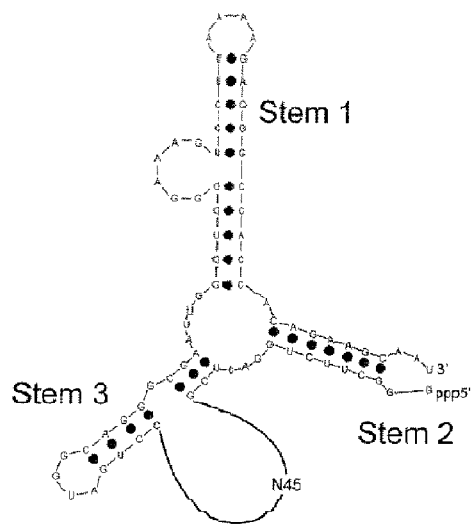
FIG. 10 is an illustration of an aptamer structure (SEQ ID NO:31) used to demonstrate allosteric selection strategy. The midstem loop, which is known to be tolerant of nucleotide additions, will be opened up and a pool of RNAs will be synthesized with 45 randomized nucleotides inserted at this position. The 5' and 3' RNA ends will be at the end of Stem 2, which maintains full function. The random nucleotide stretch (N45) is designed to provide structural flexibility for the stabilization of the core structure and also the adoption of a simple cyclic nucleotide-binding structure, which requires approximately 32 nucleotides.

One aspect of the present invention relates to a nucleic acid aptamer having a first domain that binds to a fluorescent protein.

As used herein, "nucleic acid" includes both DNA and RNA, in both D and L enantiomeric forms, as well as derivatives thereof (including, but not limited to, 2'-fluoro-, 2'-amino, 2'O-methyl, 5'iodo-, and 5'-bromo-modified polynucleotides). Nucleic acids containing modified nucleotides (Kubik et al., "Isolation and Characterization of 2'fluoro-, 2'amino-, and 2'fluoro-/amino-modified RNA Ligands or Human IFN-gamma that Inhibit Receptor Binding," *J. Immunol.* 159:259-267 (1997); Pagratis et al., "Potent 2'-amino, and 2'-fluoro-2'-deoxy-ribonucleotide RNA Inhibitors of Keratinocyte Growth Factor," *Nat. Biotechnol.* 15:68-73 (1997), which are hereby incorporated by reference in their entirety) and the L-nucleic acids (sometimes termed Spiegelmers®), enantiomeric to natural D-nucleic acids (Klussmann et al., "Mirror-image RNA that Binds D-adenosine," *Nat. Biotechnol.* 14:1112-1115 (1996) and Williams et al., "Bioactive and nuclease-resistant L-DNA Ligand of Vasopressin," *Proc. Natl. Acad. Sci. USA* 94:11285-11290 (1997), which are hereby incorporated by reference in their entirety), are used to enhance biostability.

Nucleic acid aptamers of the present invention include multivalent aptamers and bivalent aptamers. Methods of making bivalent and multivalent aptamers and their expression in multi-cellular organisms are described in U.S. Pat. No. 6,458,559 to Shi et al., which is hereby incorporated by reference in its entirety. A method for modular design and construction of multivalent nucleic acid aptamers, their expression, and methods of use are described in U.S. Patent Publication No. 2005/0282190, which is hereby incorporated by reference in its entirety. According to these methods, nucleic acid aptamers of the present invention, when minimized, can be operably joined in a single molecular entity with other aptamers or other elements, or both, in which the other elements may be structural or functional, or both.

Identifying suitable nucleic acid aptamers basically involves selecting aptamers that bind the fluorescent protein with sufficiently high affinity (e.g., $K_d$<50 nM) and specificity from a pool of nucleic acids containing a random region of varying or predetermined length (Shi et al., "A Specific RNA Hairpin Loop Structure Binds the RNA Recognition Motifs of the *Drosophila* SR Protein B52," *Mol. Cell Biol.* 17:1649-1657 (1997); Shi, "Perturbing Protein Function with RNA Aptamers," Thesis, Cornell University, University Microfilms, Inc. (1997), which are hereby incorporated by reference in their entirety).

For example, identifying suitable nucleic acid aptamers of the present invention can be carried out using an established in vitro selection and amplification scheme known as SELEX. The SELEX scheme is described in detail in U.S. Pat. No. 5,270,163 to Gold et al.; Ellington and Szostak, "In Vitro Selection of RNA Molecules that Bind Specific Ligands," *Nature* 346:818-822 (1990); and Tuerk and Gold, "Systematic Evolution of Ligands by Exponential Enrichment: RNA Ligands to Bacteriophage T4 DNA Polymerase," *Science* 249:505-510 (1990), which are hereby incorporated by reference in their entirety. The SELEX procedure can be modified so that an entire pool of aptamers with binding affinity can be identified by selectively partitioning the pool of aptamers. This procedure is described in U.S. Patent Application Publication No. 2004/0053310, which is hereby incorporated by reference in its entirety.

The fluorescent proteins capable of forming the molecular complex with the aptamer of the present invention can be any protein or polypeptide that has the ability to fluoresce. The fluorescent protein can be a naturally occurring protein or an engineered protein, such as a derivative of the naturally occurring fluorescent proteins. Exemplary fluorescent proteins include, without limitation, Aequorea-derived proteins such as GFP, enhanced Green Fluorescent Protein ("eGFP"), Yellow Fluorescent Protein ("YFP"), and Cyan Fluorescent Protein ("CFP"), as well as proteins derived from coral species including, but not limited to, *Discosoma* and *Trachyphyllia geoffroyi*. Other proteins having fluorescent or other signaling properties can also be used.

Exemplary modified fluorescent proteins include those that contain one or more of the following modifications: circular permutation (Baird et al., "Circular Permutation and Receptor Insertion Within Green Fluorescent Proteins," *Proc. Natl. Acad. Sci. USA* 96:11241-11246 (1999), which is hereby incorporated by reference in its entirety), splitting (Zhang et al., "Combinatorial Marking of Cells and Organelles with Reconstituted Fluorescent Proteins," *Cell* 119:137-144 (2004), which is hereby incorporated by reference in its entirety), enhanced folding (Pedelacq et al., "Engineering and Characterization of a Superfolder Green Fluorescent Protein," *Nat. Biotechnol.* 24:79-88 (2006), which is hereby incorporated by reference in its entirety), or other modifications (Zhang et al., "Creating New Fluorescent Probes for Cell Biology," *Nat. Rev. Mol. Cell Biol.* 3:906-918 (2002), which is hereby incorporated by reference in its entirety).

Specific examples of fluorescent proteins (and their encoding nucleic acids) are well known in the art including, without limitation, those reported as Genbank Accessions AB195239, DD431502-DD431504, DD420089-DD420091, AY013821, AY013824-AY013827, EF064258-EF064259, AF435-427-AF435-434, DQ092360-DQ092365, DQ525024-DQ525025, X83959-X83960, AY533296, AB041904, X96418, BD136947-BD136949, U73901, AX250563-AX250571, AF302837, AF183395, AF058694-AF058695, U50963, L29345, M62653-M62654, DQ301560, AY679106-AY679108, AY678264-AY678271, AF168419-AF168420, AF272711, AY786536-AY786537, AF545828, AF506025-AF506027, AF420593, BAC20344, BD440518-BD440519, and AB085641, each of which is hereby incorporated by reference in its entirety.

In a preferred embodiment, the nucleic acid aptamers of the present invention are selected based on their functional ability to interact at the first domain with the "beta cage" structure of a fluorescent protein. Both the *Aequorea victoria*-derived fluorescent proteins and the fluorescent proteins derived from coral proteins share the overall 11-stranded β can structure (Tsien, "The Green Fluorescent Protein," *Annu. Rev. Biochem.* 67:509-544 (1998); Verkhusha et al., "The Molecular Properties and Applications of Anthozoa Fluorescent Proteins and Chromoproteins," *Nat. Biotechnol.* 22:289-296 (2004), each of which is hereby incorporated by reference in its entirety).

According to one embodiment, the nucleic acid aptamers have a sequence containing a core region and one or both of a 5' primer region and a 3' primer region. The core region includes the portion of the aptamer having the first domain (i.e., fluorescent protein binding activity). The 5' and 3' primer regions are intended to provide sites to which primers can bind to the aptamer or its complement. In this manner, an aptamer population can be in vitro amplified or in vivo amplified. The 5' and 3' regions are preferably between about 15 to about 50 nucleotides in length, more preferably about 20 to about 25 nucleotides in length. The primer regions are preferably substantially unique so as to promote amplification of only (or substantially only) the aptamer sequence.

One class of exemplary nucleic acid aptamers of the present invention have a G3 nucleotide core sequence, as follows:

AUCGAAUUGUNNGGUAGAAAGUCCUUUGAGAGNAAC (SEQ ID NO: 1)
CNGGGNGGAUACUG, where N is any nucleotide (A, U, C, or G). Specific G3 core sequences may include:

AUCGAAUUGUUAGGUAGAAAGUCCUUUGAGAGGAAC (SEQ ID NO: 2)
CUGGGAGGAUACUG
and

AUCGAAUUGUGUGGUAGAAAGUCCUUUGAGAGAAAC (SEQ ID NO: 3)
CAGGGGGGAUACUG.

Another class of exemplary nucleic acid aptamers of the present invention have a G16 nucleotide core sequence, as follows:

NGNGAAUUGNGUGGGGAAAGUCCUNAAAAGAGGGCC (SEQ ID NO: 4)
ACNGCCGAAACGCC, where N is any nucleotide (A, U, C, or G). Specific G16 core sequences are identified in FIG. 2C, and include:

UGUGAAUUGGGUGGGGAAAGUCCUGAAAAGAGGGCC (SEQ ID NO: 5)
ACCGCCGAAACGCC;

UGCGAAUUGGGUGGGGAAAGUCCUGAAAAGAGGGCC (SEQ ID NO: 6)
ACCGCCGAAACGCC;

UGUGAAUUGAGUGGGGAAAGUCCUGAAAAGAGGGCC (SEQ ID NO: 7)
ACUGCCGAAACGCC;

UGUGAAUUGGGUGGGGAAAGUCCUUAAAAGAGGGCC (SEQ ID NO: 8)
ACCGCCGAAACGCC;

GGUGAAUUGGGUGGGGAAAGUCCUUAAAAGAGGGCC (SEQ ID NO: 9)
ACCGCCGAAACGCC;

UGUGAAUUGAGUGGGGAAAGUCCUGAAAAGAGGGCC (SEQ ID NO: 10)
ACCGCCGAAACGCC;
and

UGUGAAUUGAGUGGGGAAAGUCCUGAAAAGAGGGCC (SEQ ID NO: 11)
ACAGCCGAAACGCC.

Other suitable nucleotide cores may include the following sequences:
G10: GUUGGAUUGUUAGGAUAAAGC-CCGUAAAGGAGGGUCCUUAAGAGCUCCAG (SEQ ID NO: 12) and
Artificial G3, G16, G10 family derived: UUGGGGUGGGGUGGGGAAAG UCCUUAAAA-GAGGGCCACCACAGAAGCAAU (SEQ ID NO: 13) or slight variations thereof.

SEQ ID NOs: 1-13 share a predicted secondary structure, as shown in FIG. 3A (sequences include end primer sequences) having a three-way junction that connects two stems and a third stem with an apical loop and an internal loop or bulge. In FIG. 3A, the sequences from 17-66 represent the core sequences of SEQ ID NOs: 1-13. Sequence switches or substitutions that preserve the illustrated pairing preserve aptamer function, and are therefore encompassed by the present invention. This concept is further illustrated in FIG. 3B, where permutation of the core sequence at the indicated sites preserve activity, as do substitutions within the iterated sequences that conserve this secondary structure (FIG. 3C). Furthermore, additions of non-complementary sequences such as polyA sequences do not alter aptamer function and may therefore be included in the nucleic acid aptamer sequence.

Other nucleotide cores may also be developed according to the above-identified selection procedures and used according to their ability to bind fluorescent proteins. Binding of the fluorescent protein to the first domain of the nucleic acid aptamer may alter fluorescence of the fluorescent protein. In one embodiment, binding quenches fluorescence of the fluorescent protein. In an alternative embodiment, binding enhances fluorescence of the fluorescent protein. In yet another embodiment, binding does not alter fluorescence of the fluorescent protein. Accordingly, the molecular complex may have a fluorescent protein with normal fluorescence, enhanced fluorescence, or quenched fluorescence properties.

In one embodiment, the nucleotide core forms high affinity fluorescent protein binding aptamers that do not alter protein fluorescence. Exemplary aptamers possessing this characteristic include, without limitation:

```
No Quench 1: UUCGACCGAGCGAGGCCUAGAAC (SEQ ID NO: 14)
CGAGUACCAACAUAAAAAAAAAAACCGA;

No Quench 2: CGCAAAUAAUAAGAACAACAAAG (SEQ ID NO: 15)
AUGGCCUAGACAAAAACCCGGAGCGAU;

No Quench 3: CUUGAAAAAACUCCUGAAACCGA (SEQ ID NO: 16)
GGCAGAAUUAAAAACAAUUACAACAGA;

No Quench 4: CGUGCAAUGACACGCAGCGUCAA (SEQ ID NO: 17)
GACUGAGUGAUUCGACCAACGACCGCA;
and No Quench 5: GCCAGUGAGCCGAUGGAACCGAG (SEQ ID NO: 18)
GCGACUUAAAGAAAAACACAACAGAGC.
```

According to another embodiment, the nucleic acid aptamer has a sequence containing a 5' primer region, a 5' random nucleotide sequence region, a core sequence, a 3' random nucleotide sequence region, and a 3' primer region.

An exemplary nucleic acid aptamer according to this embodiment is SEQ ID NO:33, as illustrated in FIG. 4A, which has a core sequence of 36 nucleotides flanked by regions of 45 (5') and 40 (3') random nucleotides and the constant primer sequences:

```
5' primer: GGGAGCACGAUUCCAU       (SEQ ID NO: 20)
and

3' primer: UACAAGCUUCUGGACUCGGU.  (SEQ ID NO: 21)
```

The core sequence is a 36 nucleotide consensus sequence shared by families G3 and G16, as follows: GAAUUGDK-WGGKNAAAGUCCUDAAAAGAGGGCCACC (SEQ ID NO:19), where N is optional and can be G. Members of this family, designated AP2-AP8, have the following sequences (core with 5' and 3' random nucleotides) flanked by SEQ ID NOS: 20 and 21:

```
AP2 (N40→N20)
GCAAUUGUCGAGUUGUUAGCAGCAGCUUGCAUAUUG (SEQ ID NO: 22)
AGUCGUGGCGAAUUGGGUGGGGAAAGUCCUAAAAAG
AGGGCCACCACAGAGGUUUGUACCCAUAC;

AP3 (N40→N26)
GCGUGAGACGUCUUGAUGAAAUCCGGCUCGGCAAUG (SEQ ID NO: 23)
GUUCGUGGCGAAUUGGGUGGGGAAAGUCCUUAAAAG
AGGGCCACCACAGAAGCUUGUGGGAGUUAACAGCAA;

AP4
GAUUCUCGUAUCAAGGAAGGGUUAUGAGAUUUAGGU (SEQ ID NO: 24)
AAACGUGGCGAAUUGGGUGGGGAAAGUCCUAAAAAG
AGGGCCACCACAGAGGCUUGUAAUCGAUGUUACUAU
AGAGGGACACGAC;

AP5
GUAGCGUGUGGAUCAUCACCUAUGACCCGGCUACGG (SEQ ID NO: 25)
UUUCGUGGCGAAUUGGGUGGGGAAAGUCCURAAAAG
AGGGCCACCACAGAAGCCAUUUCGAAUACUCGUCCU
UGCACAGUAUCGA;

AP6
UGGAUGCCACCGCGACUACGGUUAGUAGGCAUUCUG (SEQ ID NO: 26)
AGUCGUGGCGAAUUGGGUGGGGAAAGUCCUGAAAAG
AGGGCCACCACAGAGGCUCAAACUGGACGUUAAUGA
CGUUUCGGUUCAG;

AP7
ACGGAAAGAGGUAAUUAUGCAUCUCCAAUGUGUAUG (SEQ ID NO: 27)
GUUCGUGGCGAAUUGGGUGGGGAAAGUCCUGAAAAG
AGGGCCACCACGGAAGCUUAACGGAGAGGAGCUGGG
GCGCCUUUUCCGA;
and AP8
UUUUAAUUCGCCGUGACACGUCGCGGUCAAGAAUGG (SEQ ID NO: 28)
CUUCGUGGCGAAUUGGGUGGGGAAAGUCCUGAAAAG
AGGGCCACCACAGAAGCGCUGCUUGACCAUCAAUCC
GAAUCGUCAAGUG.
```

A minimal nucleic acid aptamer (core sequence with minimal 5' and 3' primer regions and 5' and 3' random nucleotide sequence regions) was identified as:

```
GGGAGCACGAUGGCGUGGCGAAUUGGGUGGGGAAAG (SEQ ID NO: 29)
UCCUUAAAAGAGGGCCACCACAGAAGCAAUGGGCUU
CUGGACUCGGU.
```

The nucleic acid aptamer of the present invention may also have a second domain that binds to a molecule different from the fluorescent protein. Thus, the nucleic acid aptamer may have a first domain that binds to a fluorescent protein and a second domain capable of binding with a molecule other than the fluorescent protein, such as a target molecule. The target molecule can be any molecule whose presence (or absence) is of interest.

The second domain of the nucleic acid aptamer of the present invention may be a functional aptamer core that binds to a molecule other than the fluorescent protein. Suitable second domains can be identified by SELEX (described above) and then fused to aptamer structures to form multivalent aptamers having a first and second (and additional) domains.

Molecules other than the fluorescent proteins to which the second domain of the nucleic acid aptamer of the present invention may bind include any target molecule, such as natural or synthetic small molecules, macromolecules, supramolecular assemblies, or combinations thereof. In a preferred embodiment, the target molecule is a protein, nucleic acid, liposaccharide, saccharide, lipoprotein, glycoprotein, or hydrocarbon polymer. Other suitable molecular targets include small signaling molecules, cellular metabolic products, proteins that are produced by infectious agents, or oncogenic proteins.

According to a preferred embodiment, binding of the target at the second domain precludes binding, alters the binding configuration, or results in a conformation change in the nucleic acid aptamer or fluorescent protein at the first domain, thereby modulating the functional interaction of the nucleic acid aptamer with the fluorescent protein (FIGS. 1A-C). As a result, binding of the target to the second domain can result in a detectable change (e.g., a change in wavelength or intensity) in the fluorescence of the fluorescent protein. Thus, the nucleic acid aptamer of the present invention can be used as a signaling system to detect presence or location of target molecules, as described in greater detail infra.

Another aspect of the present invention relates to a molecular complex containing the nucleic acid aptamer of the present invention bound to a fluorescent protein at the first domain.

The nucleic acid aptamer is preferably reversibly bound to the fluorescent protein. Thus, the functional interaction between the nucleic acid aptamer and the fluorescent protein at the first domain can be disrupted by, e.g., conformational changes occurring in the nucleic acid aptamer and/or the fluorescent protein.

A further aspect of the present invention relates to a constructed DNA molecule containing a first region encoding a nucleic acid aptamer of the present invention and a second region encoding a fluorescent protein capable of binding to the first domain of the nucleic acid aptamer.

Preparation of the DNA Molecule can be carried out by well-known methods of DNA ligation. DNA ligation utilizes DNA ligase enzymes to covalently link or ligate fragments of DNA together by catalyzing formation of a phosphodiester bond between the 5' phosphate of one strand of DNA and the 3' hydroxyl of another. Typically, ligation reactions require a strong reducing environment and ATP. The commonly used T4 DNA ligase is an exemplary DNA ligase in preparing the DNA molecule of the present invention. Once the DNA molecule of the present invention has been constructed, it can be incorporated into cells as described infra.

Transcription of the DNA molecule of the present invention is dependent upon the presence of a promoter, which is a DNA sequence that directs the binding of RNA polymerase and thereby promotes RNA synthesis. Accordingly, the DNA molecule of the present invention may have a first promoter operably coupled to the first region to control expression of the nucleic acid aptamer and a second promoter operably coupled to the second region to control expression of the fluorescent protein. Alternatively, the DNA molecule can be bicistronic, having a single promoter that directs transcription of both the aptamer-encoding DNA sequence and the fluorescent protein.

The DNA sequences of eukaryotic promoters differ from those of prokaryotic promoters. Furthermore, eukaryotic promoters and accompanying genetic signals may not be recognized in or may not function in a prokaryotic system and, further, prokaryotic promoters are not recognized and do not function in eukaryotic cells.

Promoters vary in their "strength" (i.e., their ability to promote transcription). It is desirable to use strong promoters in order to obtain a high level of transcription. Depending upon the host cell system utilized, any one of a number of suitable promoters may be used. For instance, when cloning in E. coli, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other E. coli promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

As described above, one type of regulatory sequence is a promoter located upstream or 5' to the coding sequence of the DNA molecule. Depending upon the desired activity, it is possible to select the promoter for not only in vitro production of the nucleic acid aptamer and the fluorescent protein, but also in vivo production in cultured cells or whole organisms, as described below. Because in vivo production can be regulated genetically, a preferable type of promoter is an inducible promoter which induces transcription of the DNA molecule in response to specific conditions, thereby enabling expression of the nucleic acid aptamer and the fluorescent protein according to desired therapeutic needs (i.e., expression within specific tissues, or at specific temporal and/or developmental stages).

Preferred promoters for use with the constructed DNA molecule of the present invention include a T7 promoter, a SUP4 tRNA promoter, an RPR1 promoter, a GPD promoter, a GAL1 promoter, an hsp70 promoter, an Mtn promoter, a UAShs promoter, and functional fragments thereof. The T7 promoter is a well-defined, short DNA sequence that can be recognized and utilized by T7 RNA polymerase of the bacteriophage T7. The T7 RNA polymerase can be purified in large scale and is commercially available. The transcription reaction with T7 promoter can be conducted in vitro to produce a large amount of the molecular complex of the present invention (Milligan et al., "Oligoribonucleotide Synthesis Using T7 RNA Polymerase and Synthetic DNA Templates," Nucleic Acids Res. 15(21):8783-8798 (1987), which is hereby incorporated by reference in its entirety). The SUP4 tRNA promoter and RPR1 promoter are driven by RNA polymerase III of the yeast Saccharomyces cerevisiae, and suitable for high level expression of RNA less than 400 nucleotides in length (Kurjan et al., Mutation at the Yeast SUP4 tRNA$^{tyr}$ Locus: DNA Sequence Changes in Mutants Lacking Supressor Activity," Cell 20:701-709 (1980) and Lee et al., "Expression of RNase P RNA in Saccharomyces cerevisiae is Controlled by an Unusual RNA Polymerase III Promoter," Proc. Natl. Acad. Sci. USA 88:6986-6990 (1991), which are hereby incorporated by reference in their entirety). The glyceraldehydes-3-phosphate dehydrogenase (GPD) promoter in yeast is a strong constitutive promoter driven by RNA polymerase II (Bitter et al., "Expression of Heterologous Genes in Saccharomyces cerevisiae from Vectors Utilizing the Glyceraldehyde-3-phosphate Dehydrogenase Gene Promoter," Gene 32:263-274 (1984), which is hereby incorporated by reference in its entirety). The galactokinase (GAL1) promoter in yeast is a highly inducible promoter driven by RNA polymerase II (Johnston and Davis, "Sequences that Regulate the Divergent GAL1-GAL10 Promoter in Saccharomyces cerevisiae," Mol. Cell. Biol. 4:1440-1448 (1984), which is hereby incorporated by reference in its entirety). The heat shock promoters are heat inducible promoters driven by the RNA polymerase II in eukaryotes. The frequency with which RNA polymerase II transcribes the major heat shock genes can be increased rapidly in minutes over 100-fold upon heat shock. The heat shock promoter used in the present invention can be a Drosophila hsp70 promoter, more preferably a portion of the Drosophila hsp70 promoter which is fully functional with regard to heat inducibility and designated heat inducible cassette, or Hic (Kraus et al., "Sex-Specific Control of Drosophila melanogaster Yolk Protein 1 Gene Expression is Limited to Transcription," Mol. Cell. Biol. 8:4756-4764 (1988), which is hereby incorporated by reference in its entirety). Another inducible promoter driven by RNA polymerase II that can be used in the present invention is a metallothionine (Mtn) promoter, which is inducible to the similar degree as the heat shock promoter in a time course of hours (Stuart et al., "A 12-Base-Pair Motif that is Repeated Several Times in Metallothionine Gene Promoters Confers Metal Regulation to a Heterologous Gene," *Proc. Natl. Acad. Sci. USA* 81:7318-7322 (1984), which is hereby incorporated by reference in its entirety). An additional promoter used in the present invention is a constructed hybrid promoter in which the yeast upstream activation sequence for a GAL1 gene is fused to the core *Drosophila* hsp70 promoter (Brand and Perrimon, "Targeted Gene Expression as a Means of Altering Cell Fates and Generating Dominant Phenotypes," *Development* 118:401-415 (1993), which is hereby incorporated by reference in its entirety). This promoter is no longer activated by heat shock. Rather, it is activated by the yeast GAL4 protein, a transcription activator that is normally not present in *Drosophila*. The yeast GAL4 gene has been introduced into *Drosophila*, and is itself under a variety of transcriptional control in different fly lines.

Initiation of transcription in mammalian cells requires a suitable promoter, which may include, without limitation, β-globin, GAPDH, β-actin, actin, Cstf2t, SV40, MMTV, metallothionine-1, adenovirus E1a, CMV immediate early, immunoglobulin heavy chain promoter and enhancer, and RSV-LTR. Termination of transcription in eukaryotic genes involves cleavage at a specific site in the RNA which may precede termination of transcription. Also, eukaryotic termination varies depending on the RNA polymerase that transcribes the gene. However, selection of suitable 3' transcription termination regions is well known in the art and can be performed with routine skill.

Spatial control of an RNA molecule can be achieved by tissue-specific promoters, which have to be driven by the RNA polymerase II. The many types of cells in animals and plants are created largely through mechanisms that cause different genes to be transcribed in different cells, and many specialized animal cells can maintain their unique character when grown in culture. The tissue-specific promoters involved in such special gene switching mechanisms, which are driven by RNA polymerase II, can be used to drive the transcription templates that code for the molecular complex of the present invention, providing a means to restrict the expression of the molecular complex in particular tissues.

For gene expression in plant cells, suitable promoters may include, without limitation, nos promoter, the small subunit ribulose bisphosphate carboxylase genes, the small subunit chlorophyll A/B binding polypeptide, the $^{35}$S promoter of cauliflower mosaic virus, and promoters isolated from plant genes, including the Pto promoter itself (See C. E. Vallejos, et al., "Localization in the Tomato Genome of DNA Restriction Fragments Containing Sequences Homologous to the rRNA (45S), the major chlorophyll A/B Binding Polypeptide and the Ribulose Bisphosphate Carboxylase Genes," *Genetics* 112: 93-105 (1986) (disclosing the small subunit materials), which is hereby incorporated by reference in its entirety). The nos promoter and the 35S promoter of cauliflower mosaic virus are well known in the art.

In addition, the constructed DNA molecule may also include an operable 3' regulatory region, selected from among those which are capable of providing correct transcription termination and polyadenylation of mRNA for expression in plant cells. A number of 3' regulatory regions are known to be operable in plants. Exemplary 3' regulatory regions include, without limitation, the nopaline synthase 3' regulatory region (Fraley, et al., "Expression of Bacterial Genes in Plant Cells," *Proc. Nat'l. Acad. Sci. USA,* 80:4803-4807 (1983), which is hereby incorporated by reference in its entirety) and the cauliflower mosaic virus 3' regulatory region (Odell, et al., "Identification of DNA Sequences Required for Activity of the Cauliflower Mosaic Virus 35S Promoter," *Nature,* 313(6005): 810-812 (1985), which is hereby incorporated by reference in its entirety). Virtually any 3' regulatory region known to be operable in plants would suffice for proper expression of the coding sequence of the constructed DNA molecule of the present invention.

To obtain high level expression, the constructed DNA molecule can contain a plurality of monomeric DNA sequences ligated "head-to-tail," each of which encodes a molecular complex of the present invention (i.e., a nucleic acid aptamer having a first domain and a fluorescent protein capable of binding the nucleic acid aptamer at the first domain). This is particularly useful for augmenting the number of molecular complexes produced during each transcriptional event. By plurality, it is intended that the number of monomeric DNA sequences be at least two, preferably at least four, more preferably at least eight, and most preferably at least twelve. Such tandemly arrayed sequences are known to be relatively stable in bacteria (Lindquist, "Varying Patterns of Protein Synthesis in *Drosophila* During Heat Shock: Implications for Regulation," *Dev. Biol.* 77:463-479 (1980), which is hereby incorporated by reference in its entirety) and can persist for many generations in transgenic fly lines (Xiao and Lis, "A Consensus Sequence Polymer Inhibits In Vivo Expression of Heat Shock Genes," *Mol Cell Biol* 6:3200-3206 (1986); Shopland and Lis, "HSF Recruitment and Loss at Most *Drosophila* Heat Shock Loci is Coordinated and Depends on Proximal Promoter Sequences," *Chromosoma* 105:158-171 (1996), which are hereby incorporated by reference in their entirety). This strategy should be applicable to other organisms. For example, long direct repeating sequences have been used in yeast (Robinett et al., "In Vivo Localization of DNA Sequences and Visualization of Largescale Chromatin Organization Using lac Operator/Repressor Recognition," *J. Cell Biol.* 135:1685-700 (1996), which is hereby incorporated by reference in its entirety). It should be apparent to those of ordinary skill in the art, however, that the number of monomeric DNA sequences can vary for each application of the DNA molecule.

Depending upon the desired application and intended use for the DNA molecule, it is possible to produce homopolymers containing a plurality of substantially identical monomeric DNA sequences or copolymers containing a plurality of substantially different monomeric DNA sequences. It is also possible to produce copolymers, block polymers, or combinations thereof, that contain a plurality of substantially different monomeric DNA sequences. The molecular complexes produced from such a homopolymer are a single type. In contrast, the molecular complexes produced from such a copolymer, a block polymer, or a combination thereof, are different types (i.e., expressing different aptamers, different fluorescent proteins, or both). Thus, the plurality of monomeric DNA sequences can be substantially identical (i.e., producing substantially the same molecular complex) or they can be substantially different (i.e., producing substantially different molecular complexes). When the plurality of monomeric DNA sequences are substantially different, the resulting molecular complexes can be directed to the same or to different target molecules.

When the DNA molecule encodes a plurality of molecular complex sequences, it is important that the resulting RNA transcript be cleaved into individual RNA molecules corresponding to the molecular complexes of the present invention. To this end, it is particularly desirable for each of the plurality of monomeric DNA sequences to also encode a cis-acting ribozyme that can cleave the RNA transcript of the DNA molecule to yield multiple copies of the RNA molecule giving rise to the molecular complexes. Although any ribozyme sequence can be utilized, a hammerhead ribozyme sequence (Haseloff and Gerlach, "Simple RNA Enzymes with New and High Specific Endoribonucleases Activities," Nature 334:585-591 (1988), which is hereby incorporated by reference in its entirety) is preferred because of its simplified and efficient structure. The sequence encoding the hammerhead ribozyme is incorporated into each of the plurality of monomeric DNA sequences, resulting in the hammerhead ribozyme being located at one end of each monomeric unit of the immature RNA transcript. The immature RNA transcript is self-cleaved by the cis-acting ribozyme.

Once the DNA molecule of the present invention has been constructed, it can be incorporated into cells using conventional recombinant DNA technology. Generally, this involves inserting the DNA molecule into an expression system to which the DNA molecule is heterologous (i.e., not normally present). The heterologous DNA molecule is inserted into the expression system or vector in proper sense orientation. The vector contains the necessary elements for their persistent existence inside cells and for the transcription of an RNA molecule that can be translated into the molecular complex of the present invention.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and transfection, and replicated in cultures including prokaryotic organisms and eukaryotic cells grown in tissue culture.

Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference), pQE, pIH821, pGEX, pET series (see Studier et. al., "Use of T7 RNA Polymerase to Direct Expression of Cloned Genes," *Gene Expression Technology*, vol. 185 (1990), which is hereby incorporated by reference in its entirety), pIIIEx426 RPR, pIIIEx426 tRNA (see Good and Engelke, "Yeast Expression Vectors Using RNA Polymerase III Promoters," *Gene* 151:209-214 (1994), which is hereby incorporated by reference in its entirety), p426GPD (see Mumberg et al., "Yeast Vectors for the Controlled Expression of Heterologous Proteins in Different Genetic Background," *Gene* 156:119-122 (1995), which is hereby incorporated by reference in its entirety), p426GAL1 (see Mumberg et al., "Regulatable Promoters of *Saccharomyces cerevisiae*: Comparison of Transcriptional Activity and Their Use for Heterologous Expression," *Nucleic Acids Research* 22:5767-5768 (1994), which is hereby incorporated by reference in its entirety), pUAST (see Brand and Perrimon, "Targeted Gene Expression as a Means of Altering Cell Fates and Generating Dominant Phenotypes," *Development* 118: 401-415 (1993), which is hereby incorporated by reference in its entirety), and any derivatives thereof. Suitable vectors are continually being developed and identified.

A variety of host-vector systems may be utilized to express the DNA molecule. Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, adeno-associated virus, retroviral vectors, etc.); insect cell systems infected with virus (e.g., baculovirus); and plant cells infected by bacteria or transformed via particle bombardment (i.e., biolistics). The expression elements of these vectors vary in their strength and specificities. Depending upon the host-vector system utilized, any one of a number of suitable transcription elements can be used.

Once the constructed DNA molecule has been cloned into an expression system, it is ready to be incorporated into a host cell. Such incorporation can be carried out by the various forms of transformation, depending upon the vector/host cell system such as transformation, transduction, conjugation, mobilization, or electroporation. The DNA sequences are cloned into the vector using standard cloning procedures in the art, as described by Maniatis et al., *Molecular Cloning: A Laboratory Manual*, Cold Springs Laboratory, Cold Springs Harbor, N.Y. (1982), which is hereby incorporated by reference in its entirety. Suitable host cells include, but are not limited to, bacteria, yeast, mammalian cells, insect cells, plant cells, and the like. The host cell is preferably present either in a cell culture (ex vivo) or in a whole living organism (in vivo).

Mammalian cells suitable for carrying out the present invention include, without limitation, COS (e.g., ATCC No. CRL 1650 or 1651), BHK (e.g., ATCC No. CRL 6281), CHO (ATCC No. CCL 61), HeLa (e.g., ATCC No. CCL 2), 293 (ATCC No. 1573), CHOP, NS-1 cells, and primary cells recovered directly from a mammalian organism. With regard to primary cells recovered from a mammalian organism, these cells can optionally be reintroduced into the mammal from which they were harvested.

The expression of high levels of functional RNA aptamers within cells can be complicated by several factors including RNA stability, short half-life, and difficulties in cellular targeting. Nonetheless, substantial progress has been achieved over the last several years. The first demonstration of aptamer function in live cells involved nuclear targets (Klug et al., "In Vitro and In Vivo Characterization of Novel mRNA Motifs that Bind Special Elongation Factor SelB," *Proc. Natl. Acad. Sci. USA* 94:6676-6681 (1997); Shi et al., "RNA Aptamers as Effective Protein Antagonists In a Multicellular Organism," *Proc. Natl. Acad. Sci. USA* 96:10033-10038 (1999); Thomas et al., "Selective Targeting and Inhibition of Yeast RNA Polymerase II by RNA Aptamers," *J. Biol. Chem.* 272: 27980-27986 (1997), which are hereby incorporated by reference in their entirety). It has been demonstrated, for example, that the RNAs directed against the *Drosophila* B52 protein inhibit B52 function and suppresses the phenotype of B52 overexpression in transgenic flies, and have pioneered the use of concatameric genetic constructs that undergo self cleavage following transcription (Shi et al., "RNA Aptamers as Effective Protein Antagonists In a Multicellular Organism," *Proc. Natl. Acad. Sci. USA* 96:10033-10038 (1999), which is hereby incorporated by reference in its entirety). Aptamer function within the nucleus of mammalian cells has also been demonstrated (Symensma et al., "Polyvalent Rev Decoys Act as Artificial Rev-Responsive Elements," *J. Virol.* 73:4341-4349 (1999), which is hereby incorporated by reference in its entirety). More recently, effective strategies for cytoplasmic targeting of aptamer have also been developed. For example, the human tRNA initiator sequence, which mediates highly efficient nuclear export to deliver functional chimeric RNA aptamers to the cytosol has been used (Chaloin et al., "Endogenous Expression of a High-Affinity Pseudoknot RNA Aptamer Suppresses Replication of HIV-1," *Nucleic Acids Res.* 30: 4001-4008 (2002), which is hereby incorporated by reference in its entirety). Functional RNA aptamers have also been directly delivered to the cytoplasm by lipofection (Theis et al., "Discriminatory Aptamer Reveals Serum Response Element Transcription Regulated by Cytohesin-2," *Proc. Natl. Acad. Sci. USA* 101:11221-11226 (2004), which is hereby incorporated by reference in its entirety). Finally, most recently, very high levels of aptamer expression ($1 \times 10^7$ molecules per cell) have been achieved by fusion with a highly stable transcript (Choi et al., "Intracellular Expression of the T-cell Factor-1 RNA Aptamer as an Intramer," *Mol Cancer Ther.* 5:2428-2434 (2006), which is hereby incorporated by reference in its entirety). The use of chimeric RNAs and other strategies will be systematically explored to achieve high levels of nuclear and cytoplasmic FQA expression.

Plant tissues suitable for transformation include leaf tissue, root tissue, meristems, zygotic and somatic embryos, and anthers. It is particularly preferred to utilize embryos obtained from anther cultures. The expression system of the present invention can be used to transform virtually any plant tissue under suitable conditions, and the transformed cells can be regenerated into whole plants.

One approach to transforming plant cells and/or plant cell cultures, tissues, suspensions, etc. with a DNA molecule of the present invention is particle bombardment (also known as biolistic transformation) of the host cell. This technique is disclosed in U.S. Pat. Nos. 4,945,050, 5,036,006, and 5,100,792, all to Sanford, et al., which are hereby incorporated by reference in their entirety.

Another method of introducing DNA molecules into a host cell is fusion of protoplasts with other entities, either minicells, cells, lysosomes, or other fusible lipid-surfaced bodies that contain the DNA molecule (Fraley et al., "Expression of Bacterial Genes in Plant Cells," *Proc. Natl. Acad. Sci. USA* 80:4803-4807 (1983), which is hereby incorporated by reference in its entirety).

The DNA molecule of the present invention may also be introduced into the plant cells and/or plant cell cultures, tissues, suspensions, etc. by electroporation (Fromm et al., "Expression of Genes Transferred into Monocot and Dicot Plant Cells by Electroporation," *Proc. Natl. Acad. Sci. USA* 82:5824 (1985), which is hereby incorporated by reference in its entirety).

In producing transgenic plants, the DNA construct in a vector described above can be microinjected directly into plant cells by use of micropipettes to transfer mechanically the recombinant DNA (Crossway, "Integration of Foreign DNA Following Microinjection of Tobacco Mesophyll Protoplasts," *Mol. Gen. Genetics* 202:179-85 (1985), which is hereby incorporated by reference in its entirety). The genetic material may also be transferred into the plant cell using polyethylene glycol (Krens et al., "In Vitro Transformation of Plant Protoplasts with TI-Plasmid DNA," *Nature* 296:72-74 (1982), which is hereby incorporated by reference in its entirety).

One technique of transforming plants with the DNA molecules in accordance with the present invention is by contacting the tissue of such plants with an inoculum of a bacteria transformed with a vector comprising a DNA molecule in accordance with the present invention. Generally, this procedure involves inoculating the plant tissue with a suspension of bacteria and incubating the tissue for 48 to 72 hours on regeneration medium without antibiotics at 25-28° C.

Bacteria from the genus *Agrobacterium* can be utilized to transform plant cells. Suitable species of such bacterium include *Agrobacterium tumefaciens* and *Agrobacterium rhizogenes*. *Agrobacterium tumefaciens* (e.g., strains C58, LBA4404, or EHA105) is particularly useful due to its well-known ability to transform plants.

Heterologous genetic sequences can be introduced into appropriate plant cells by means of the Ti plasmid of *A. tumefaciens* or the Ri plasmid of *A. rhizogenes*. The Ti or Ri plasmid is transmitted to plant cells on infection by *Agrobacterium* and is stably integrated into the plant genome (Schell, "Transgenic Plants as Tools to Study the Molecular Organization of Plant Genes," *Science* 237:1176-83 (1987), which is hereby incorporated by reference in its entirety).

After transformation, the transformed plant cells must be regenerated.

Plant regeneration from cultured protoplasts is described in Evans et al., *Handbook of Plant Cell Cultures, Vol. 1*, MacMillan Publishing Co., New York (1983) and Vasil (ed.), *Cell Culture and Somatic Cell Genetics of Plants*, Acad. Press, Orlando, Vol. I (1984) and Vol. III (1986), which are hereby incorporated by reference.

It is known that practically all plants can be regenerated from cultured cells or tissues.

Another aspect of the present invention relates to a system containing a first DNA molecule encoding a nucleic acid aptamer as described above and a second DNA molecule encoding a fluorescent protein capable of being bound by the first domain. In a preferred embodiment of the system, the first and second DNA molecules each have a promoter operably coupled to the regions encoding, respectively, the nucleic acid aptamer and the fluorescent protein. The system of the invention may be incorporated into expression systems and/or host cells as described supra.

A further aspect of the present invention relates to a method of detecting a molecular target. This method involves providing a molecular complex as described above and contacting a molecular target with the molecular complex under conditions effective to cause a change in fluorescence of the fluorescent protein (i.e., upon binding of the target to the second domain of the aptamer). As a consequence, the change in fluorescence indicates (i.e., allows detection of) presence of the molecular target.

The method of the invention may be carried out in a cell by introducing the molecular complex into the cell. In one embodiment, the complex is recombinantly expressed in a cell. Methods for introducing the molecular complex into a cell are described supra.

Contacting a target with the molecular complex of the present invention at the second domain can modulate binding of fluorescent protein at the first domain, inhibit binding of the fluorescent protein at the first domain, alter the binding configuration of the fluorescent protein at the first domain, or cause a conformational change in the nucleic acid aptamer or fluorescent protein that alters binding of the fluorescent protein at the first domain. As a result, the functional interaction of the nucleic acid aptamer with the fluorescent protein can be altered and thereby result in a detectable change in fluorescence (e.g., a shift in the fluorescence wavelength or intensity) of the fluorescent protein. Accordingly, by this method, one can detect when the molecular complex of the present invention contacts a target molecule.

Detecting a change in fluorescence may be carried out by visual observation. Alternatively, detecting a change in fluorescence may be carried out with a spectrophotometer, or a microscope or macroscope system coupled to a camera or photomultiplier tube. Coupled with proper instrumentation, the optical readout can be followed in real time in living systems to obtain spatio-temporal information (functional intracellular imaging).

By way of example, if the molecular complex employed in the method of the present invention quenches fluorescence of the fluorescent protein when the fluorescent protein is bound to the first domain, contacting the molecular complex with a target molecule at the second domain may cause a change in the functional interaction of the nucleic acid aptamer with the fluorescent protein at the first domain which results in an unquenched fluorescence signal (i.e., the fluorescence of the fluorescent protein is no longer quenched).

In another example, if the molecular complex employed in the method of the present invention enhances fluorescence of the fluorescent protein when the fluorescent protein is bound to the first domain, contacting the molecular complex with a target molecule at the second domain may cause a change in the functional interaction of the nucleic acid aptamer with the fluorescent protein at the first domain which results in a decreased fluorescence signal (i.e., the fluorescence of the fluorescent protein is no longer enhanced).

In yet another example, if the molecular complex employed in the method of the present invention does not alter the fluorescence of the fluorescent protein when the fluorescent protein is bound to the first domain, contacting the molecular complex with a target molecule at the second domain may cause a change in the functional interaction of the nucleic acid aptamer with the fluorescent protein at the first domain which results in an altered fluorescence signal.

Another aspect of the present invention relates to a method of determining location of a molecular target. This method involves providing a molecular complex as described above. A molecular target is contacted with the molecular complex and the fluorescence of the fluorescent protein is detected, whereby location of the molecular target is determined.

These aspects of the present invention are further illustrated by the examples below.

EXAMPLES

The following examples are provided to illustrate embodiments of the present invention, but they are by no means intended to limit its scope.

Example 1

Development of Fluorescence Quenching Aptamers

A large RNA pool of randomized 50 nucleotides containing an estimated $10^{14}$-$10^{16}$ unique molecules was screened using a traditional selection scheme that relied on the immobilization of GFP on nitrocellulose membrane, as well as a negative selection step to remove membrane binding species. This strategy was not successful, as multiple selection rounds resulted in highly enriched multi-G species and poor GFP specific binding. These results occurred despite negative selection throughout the selection process, consistent with the selection of nitrocellulose membrane binding (multi-G) motifs and the incorporation of repeated ribonuclease H(RNase H) digestion steps, which did not markedly improve the selection of species demonstrating specific GFP binding (Shi et al., "Evolutionary Dynamics and Population Control During In Vitro Selection and Amplification with Multiple Targets," RNA 8:1461-1470 (2002), which is hererby incorporated by reference in its entirety). Parallel selection using a circularly permutate GFP protein resulted in excellent enrichment. This complication may result from the low surface complexity of the 11β-strand "can" structure of GFP and explains previously unsuccessful attempts to isolate aptamers with high affinity to GFP (Stanlis et al., "Single-strand DNA Aptamers as Probes for Protein Localization in Cells," J. Histochem. Cytochem. 51:797-808 (2003), which is hereby incorporated by reference in its entirety).

To overcome this problem, selection rounds were alternated by using His-tagged GFP bound to Ni-charged beads and nitrocellulose membrane-bound GFP in the selection step. Negative selection with nitrocellulose membrane or Ni-charged beads was also employed at each step. This procedure resulted in strong selection pressure on the RNA pool and, following 15 iterations of binding and amplification, the sequenced RNA pool consisted of multiple copies of 2 highly related families, both of which displayed submicromolar binding affinity in a nitrocellulose membrane binding assay (FIG. 2A). The higher affinity family (G16) decreased GFP/eGFP fluorescence in a concentration dependent manner in physiological buffer with a $K_D$ of approximately 30 nM (FIG. 2B), consistent with the observation of a progressive loss of fluorescence of the immobilized GFP during the iterative aptamer binding steps of the selection. The selected RNAs were highly related, falling in two general families, which were themselves homologous (FIG. 2C). The total size of the functional aptamers was 100 nt, as 25 nt fixed PCR primers were included on either side of the selected 50 nt core. Truncation of G16 by removal of either the 5' or 3' PCR primer regions resulted in a loss of activity, indicating that these 5' and 3' sequences were necessary for the functional secondary structure.

Using information on the core binding structure described above, a second pool of RNAs was designed that included the core 36 nt binding sequence shared by families G3 and G16 (SEQ ID NO: 19), flanked by variable regions of 45 (5') and 40 (3') nucleotides and the constant PCR primer sequences (FIG. 4A). This pool of $10^{14}$-$10^{16}$ unique RNAs was subjected to 12 SELEX amplification rounds using alternating membrane and bead selection steps. As shown in FIGS. 4B-C, clones from this selection showed distinctly higher binding affinity than G16, the most effective sequence from the initial selection. Sequencing of individual clones again revealed multiple copies of individual sequences, with the two most abundant clones having been mutated and shortened within the 3' random sequence, either due to rare copies of shortened template DNA in the original pool or to PCR errors. One of these clones, AP3 (SEQ ID NO: 23, with primers SEQ ID NOS: 20 and 21), showed the highest affinity ($K_D$=14.4 nM) and efficacy (70% inhibition) of GFP fluorescence inhibition (FIG. 4D).

Example 2

Effect on Other Fluorescent Proteins

The Aequorea victoria-derived fluorescent proteins are highly homologous at the level of sequence and overall structure (Tsien, "The Green Fluorescent Protein," Ann. Rev. Biochem. 67:509-544 (1998), which is hereby incorporated by reference in its entirety). Thus, eYFP differs by only 5 residues and eCFP by only 4 residues, relative to eGFP. Moreover, fluorescent proteins derived from coral proteins also share the overall 11-stranded β can structure, despite substantial sequence diversity (Verkhusha et al., "The Molecular Properties and Applications of Anthozoa Fluorescent Proteins and Chromoproteins," Nat. Biotechnol. 22:289-296) (2004), which is hereby incorporated by reference in its entirety). It was then determined whether the high affinity aptamers, selected by binding to GFP, would bind to and inhibit the fluorescence of other fluorescent proteins. As shown in FIG. 5A, AP3 binds with roughly equivalent affinity to GFP, eGFP, eCFP, and eYFP. Surprisingly, however, aptamer binding enhances the eCFP and eYFP fluorescence (FIG. 5B). Measurements of absorbance of these proteins in the presence of aptamer confirmed a distinct effect on GFP/eGFP, in that aptamer binding markedly reduced absorption of photons at peak excitation wavelengths, whereas this was not true for the other fluorescent proteins (FIG. 5C). The pre-selected aptamer pool had no effect on fluorescence of any proteins. Lower affinity binding of AP3 to the more distantly related Azumi green protein was observed.

Example 3

Mechanism of Fluorescence Quenching

Given the selective and potent effect of fluorescence quenching aptamers ("FQA"), the effect of aptamer binding on GFP photophysics was investigated. One possible explanation for the observed effect would be a shift in the relative absorption peaks between the protonated (397 nm) and unprotonated (470 nm) forms of the GFP molecule, which account for the well known pH sensitivity of the 470 nm fluorescence. The ionization state is modulated by a proton network, comprising an intricate network of polar interactions between the chromophore and several surrounding amino acids. Aptamer binding could either be changing the pKa of wtGFP or be binding in a manner that mimics protonation. Either mechanism could result in a change in the relative proportions of each species at a constant pH.

Emission scans indicate, however, that there is no significant difference in fluorescence exciting at 390 nm, despite a 74% decrease in 470 nm excited fluorescence (FIGS. 6A-C). This finding is also consistent with the effect of the aptamer on eGFP, which has a markedly reduced 390 nm absorption peak compared to the wild type form of the protein. Quantitative measurements of the effect of AP3 RNA on the absorption spectra of GFP indicated a 50% decrease in absorption at 475 nm ($\epsilon$=6000 $M^{-1}$ $cm^{-1}$) yet only a 10% increase in the 397 nm ($\epsilon$=25000 $M^{-1}$ $cm^{-1}$) (Magde et al., "Fluorescence Quantum Yields and Their Relation to Lifetimes of Rhodamine 6G and Fluorescein in Nine Solvents: Improved Absolute Standards for Quantum Yields," *Photochem. Photobiol.* 75:327-334 (2002), which is hereby incorporated by reference in its entirety).

If only a simple change in the relative proportion of the two states is involved, a concurrent 50% increase in the 390 nm absorption would be expected. In addition, the 50% absorption decrease at 470 nm does not completely account for the 74% decrease seen in 470 nm excited fluorescence, indicating that the aptamer-bound GFP species has different absorption and different fluorescence properties than free GFP. Bulk quantum yields under 470 nm excitation (referenced to fluorescein in 0.1N NaOH; $\phi$=0.925) (Wang et al., "Unnatural Amino Acid Mutagenesis of Green Fluorescent Protein," *J. Org. Chem.* 68:174-176 (2003), which is hereby incorporated by reference in its entirety), indicated ~66% decrease, but no change in quantum yield when using 390 nm excitation. These results are consistent with the fluorescence changes seen. Interestingly, an initial measurement of fluorescence lifetimes showed that they were identical in the presence of the aptamer (~2.7 ns), indicating no evidence of direct quenching of the excited state by the aptamer. A caveat of these measurements is that the data were obtained using two-photon excitation at 880 nm (and 780 nm) and may not be relevant since the initial excited state populated in two-photon absorption process is not the same as with single photon excitation. Based on preliminary results, one interpretation is that the aptamer binds to both forms of GFP and has different effects on each species. For the species of interest (470 nm unprotonated form) binding may alter the conformation of GFP in a manner that both reduces the absorption, possibly by altering the transition dipole, as well causing a reduction in the quantum yield (e.g., increases the radiationless decay route).

Example 4

Dual Wavelength Measurements

As shown in FIGS. 6A-C, aptamer binding to GFP results in minimal changes in the fluorescence of the 390 nm-excited molecule, suggesting a strategy for dual wavelength fluorescence measurements that would be independent of fluorophore concentration or effective fluorescence pathlength. As shown in FIGS. 7A-C, aptamer binding to GFP results in a small increase in the 390 nm fluorescence in addition to the marked decrease in 470 nm fluorescence, with an isosbestic point at 426 nm (see also FIGS. 6A-C). Aptamer binding to GFP results in a consistent fractional drop in fluorescence that is independent of the concentration of the fluorophore (FIG. 7D). The 470/426 nm ratio preserves the approximately 3 fold dynamic range of the interaction. It was found that the 470/390 nm fluorescence ratio was slightly less consistent.

Example 5

Aptamer Secondary Structure

The structure for GFP aptamers has been further refined by identifying the core sequence underlying activity, creating a new RNA pool with this sequence and random flanking nucleotides (40 mers), and re-selecting. This process led to the identification of several sequences of different length, with identical high binding affinity. The common predicted secondary structure of these RNAs was three short stems around a central loop (FIG. 8A), with structures varying as to the length of the stems. Through a series of substitutions, each stem was minimized until binding/fluorescence activity was lost. For example, RNAs with full function contained sequences with predicted Stem 2 of variable length (up to 11 pairs); decreasing this stem to 7 pairs retained full function, but a 6 pair stem achieved only a 45% decrease in GFP fluorescence. Also, within Stem 2, the sequence of the first 6 pairs (numbering from the end of the stem inward) could be substituted with no loss in function, whereas the changes in the C-G pair at the internal loop resulted in a slight decrease in function.

Following minimization of the stem lengths, the base pairing was confirmed by selected substitutions that destabilized specific stems. For example, in Stem 3, the addition of paired nucleotides between positions 20/21 and 79/80 resulted in full function (dotted circle in FIG. 8A), whereas single nucleotide additions at these positions destroyed function, confirming the secondary structure in this region. Similar paired substitutions were performed in Stem 2. Insertions within the central loop resulted in full function, although the angle between loops 1 and 2 (arrow FIG. 8A) was critical and insertion of a single nucleotide resulted in 50% fluorescence quench. Circular permutation of the structures indicated that they could be opened at the ends of Stem 2 or Stem 3, further confirming this structure. Importantly, addition of nucleotides from the open loop of Stem 2 retained full function. Finally, the structure of Stem 3 was further confirmed by encoding from Stem 2, randomizing the nucleotides comprising Stem 3, and performing SELEX. This process led to the identification of 24 highly related sequences, each of which consisted of two stems separated by a variation of the closed loop contained within Stem 3 (FIG. 8B). These experiments establish the 2° structure of FQAs and provide feasibility for the creation of allosterically regulated aptamers, as they have identified the minimal functional structures and the retention of this function when the aptamers are opened and elongated.

Prophetic Example 6

Developing Genetic Systems for the Balanced Expression of GFP and Aptamer RNA in the Nucleus and Cytosol of Mammalian Cells Genetically encoded sensors of cell signaling have distinct advantages as expression of these molecules can be tightly controlled and subcellularly localized. To date, these sensors have been constructed from polypeptides, exploiting the binding characteristics of specific peptide domains (detector) to alter protein fluorescence (reporter) either directly or through resonance energy transfer. In the case of FRET sensors, usually the detector consists of peptide elements with high affinity that bring the donor and acceptor reporter fluorophores into proximity sufficient for energy transfer. There are several disadvantages to this approach. First, reliance on specific protein binding motifs requires de novo design and optimization of each sensor, a process that is time consuming and often unsuccessful due to the requirement to effectively couple the conformational change of the detector to alterations in the reporter. Second, binding of other proteins to the sensor (detector or reporter) may markedly alter its characteristics, an outcome made more likely by the use of peptide elements that have evolved to interact with other cellular partners. Thus, cellular elements that bind, for example, to uncharacterized components of the detector can markedly alter its behavior in a living cell. Finally, detection of a target requires a known binding partner of appropriate affinity and specificity. However, in many cases such a detector motif is not known. Examples of this difficulty include the detection of specific phosphoproteins for which hundreds of variants may exist and the detection of aberrantly-folded proteins for which no known binding partners exist.

An alternative strategy relies on the use of structural RNAs as relatively simple fluorescent switches. The affinity of RNA aptamers to fluorescent proteins will be regulated by the binding of a molecule to be detected. This binding will perturb the highly specific structural interaction between the aptamer and fluorescent protein, thereby resulting in unbinding and a fluorescent signal proportional to the concentration of the analyte. The use of FQAs as a flexible, genetically encoded, real time detector system will be investigated and genetic expression methods and allosteric switches that are required to realize the potential of this system will be developed. Given the extreme size and diversity of the aptamer structural space, this strategy may enable the development of sensors for virtually any defined target.

A fundamental requirement for the development of the proposed RNA/fluorescent protein sensor system is the efficient and balanced expression of RNA and GFP. Efficient genetic expression systems will be developed for FQAs and their function in live cells will be assessed. The development of functional, chimeric RNAs will be useful both for the expression of the GFP signaling system (infra) and as a means of localizing YFP or CFP to non-protein biological molecules, as the chromaphores are not quenched by binding.

Experiments will be conducted in stable HEK293T cell lines in which GFP or GFP flanked by a nuclear localization signal are stably expressed. These lines have been developed through transfection of cells with bicistronic mammalian expression vectors that include GFP and the neomycin resistance cassette under control of a strong viral promoter (CMV). Cells have been selected with neomycin and clones established that display a modest and stable degree of cytoplasmic or nuclear GFP expression. This strategy eliminates difficulties related to the kinetics of RNA and protein expression in transient transfection assays.

HEK293T cells will be transfected in 6 well plates with varying concentrations of vector DNA prepared from bicistronic constructs encoding chimeric RNAs and an mCherry reporter that will serve as a marker for gene transfer. These cells will be transfected with the vector DNA using LipofectAMINE PLUS™ reagent (Life Technologies, Invitrogen Corporation, Carlsbad, Calif.).

The chimeric aptamer constructs described below will be driven by RNA polymerase III promoters, which have been shown to direct high concentrations of siRNA in cells and mice (Yu et al., "Reproducible and Inducible Knockdown of Gene Expression in Mice," *Genesis* 44:252-261 (2006), which is hereby incorporated by reference in its entirety). The chimeric systems to be used are:

U6 small nuclear RNA (snRNA) promoter and related adapter sequences for nuclear expression of the GFP aptamer (FIGS. 9A-B);

the 5S ribosomal RNA promoter and 5S RNA sequences for cytoplasmic expression (these RNA sequences mediate protein binding and nuclear export) (FIGS. 9C-D);

the 7SL RNA promoter and signal recognition particle sequences for cytoplasmic expression (FIGS. 9E-F);

a chimeric construct containing flanking tRNA methionine sequences previously shown to efficiently direct RNA aptamer nuclear export (Chaloin et al., "Endogenous Expression of a High-Affinity Pseudoknot RNA Aptamer Suppresses Replication of HIV-1," *Nucleic Acids Res.* 30:4001-4008 (2002); Thompson et al., "Improved Accumulation and Activity of Ribozymes Expressed From a tRNA-Based RNA Polymerase III Promoter," *Nucleic Acids Res.* 23:2259-2268 (1995), which are hereby incorporated by reference in their entirety) (the tRNA sequence directs transcription) (FIGS. 9G-H); and a second tRNA construct using the valine tRNA flanking sequence (FIG. 9I).

The adapter RNA sequences are included to provide stability, correct folding, and nuclear export. All chimeric RNAs have been synthesized and their function has been confirmed in binding and fluorecence assays in vitro.

The degree of RNA expression in the nucleus and cytoplasm of cells will be quantitatively examined following flow cytometric sorting of mCherry positive cells. At the time of analysis (initially 12, 24, 36, and 48 h post-transfection), cells will be incubated in buffer containing 50 mM Tris HCl pH 8.0, 140 mM NaCl, 1 mM DTT, 1.5 mM $MgCl_2$ and 0.5% (v/v) NP-40 for 5 min on ice. Cytoplasmic RNA will be separated from nuclear RNA by centrifugation (2 min at 300 g and 4° C.). Supernatant containing the cytoplasmic fraction and pellets containing the nuclear fraction will be incubated with Trizol reagent and RNA purification performed. The amount of RNA in each sample will be determined by $OD_{260}$ measurements. RNA samples will be subjected to electrophoresis in formaldehyde agarose gels (1.2%), transferred to a nylon membrane (Hybond N+, Amersham Pharmacia Biotech) and hybridized with $^{32}$P-labeled probes for the GFP aptamer, chimeric RNA, tRNA$^{val}$, tRNA$^{met}$, 7SL, 5S, or U6 snRNA probes (pseudoknot, tRNA$^{Lys3}$ or U6 snRNA). Membranes will be extensively washed and imaged on a phosphorimager (Fuji FLA 3000 radioluminograph scanner). Cytoplasmic RNA and nuclear RNA will also be assayed by Real-time RT-PCR using SYBR Green I. RNA will be briefly exposed to RNAase-free DNAase I and 1 µg reverse transcribed to cDNA using chimeric RNA-specific primers and Thermoscript RT (Invitrogen, Carlsbad, Calif.). U6 and 18S RNA will be used as the endogenous control. The real-time PCR reaction mixture (25 µl) with SYBR Green I will be amplified using an iCycler iQ Real-time PCR Detection System (BIO-RAD). PCR specificity will be examined by electrophoresis on a 2% agarose gel.

The function of the RNA aptamers will be determined by assessing GFP fluorescence in mCherry-positive cells during flow cytometry.

Prophetic Example 7

Selection of RNA Aptamers that Bind to the Target Molecule (cGMP) and Alter the RNA Affinity to GFP As a proof-of-principle for the use of FQAs as intracellular sensors, it will be attempted to control the affinity of the aptamers to GFP by the binding of a second molecule, thereby creating fluorescent switches or detectors. This will be enhanced by minimization of the sequence length and further information about the critical secondary structure. However, it is believed that selection should yield regulatable aptamers, as this only requires two simple conditions: (1) addition of a second binding motif/structure and (2) requirement that binding of the second molecule results in an allosteric interaction that alters the tertiary structure of the molecule. The first condition is routinely achieved through SELEX procedures and the second can be incorporated into the selection scheme. However, we will also attempt to forward design the switch using approaches that have proved successful for smaller aptamers (Breaker et al., "Inventing and Improving Ribozyme Function: Rational Design Versus Iterative Selection Methods," *Trends Biotechnol.* 12:268-275 (1994); Koizumi et al., "Allosteric Ribozymes Sensitive to the Second Messengers cAMP and cGMP," *Nucleic Acids Symp. Ser.* 275-276 (1999); Soukup et al., "Engineering Precision RNA Molecular Switches," *Proc. Natl. Acad. Sci. USA* 96:3584-3589 (1999); Stojanovic et al., "Modular Aptameric Sensors," *J. Am. Chem. Soc.* 126:9266-9270 (2004), which are hereby incorporated by reference in their entirety). cGMP is an important intracellular second messenger for which existing sensors have distinct limitations (Wild et al., "Expression of a Chimeric, cGMP-Sensitive Regulatory Subunit of the cAMP-Dependent Protein Kinase Type I Alpha,"*FEBS Letters* 374: 356-362 (1995). Aptamers for cGMP will be used, as well as one for which allosterically regulated RNA aptamers have been successfully selected (Koizumi et al., "Allosteric Ribozymes Sensitive to the Second Messengers cAMP and cGMP," *Nucleic Acids Symp. Ser.* 275-276 (1999); Koizumi et al., "Allosteric Selection of Ribozymes that Respond to the Second Messengers cGMP and cAMP," *Nat. Struct. Biol.* 6:1062-1071 (1999), which are hereby incorporated by reference in their entirety).

Figure 11:
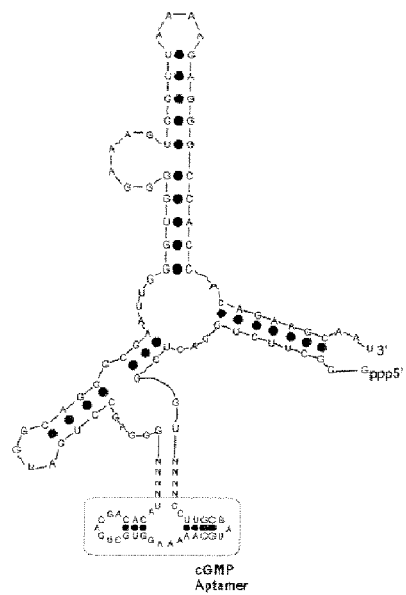
FIG. 11 is an illustration of an aptamer structure (SEQ ID NO:32) used to demonstrate allosteric selection of a bridge domain. The cGMP aptamer sequence will be separated by a short stretch of randomized sequences sufficient to optimize the allosteric bridge (24) (N indicates random nucleotide).

Allosteric selection of the core fluorescence quenching protein sequence will start with an RNA pool that contains random nucleotides attached to the minimum GFP-binding core sequence that was determined (FIG. 10). To maximize the likelihood of obtaining allosteric linkage to the reporter (GFP binding) region, this core structure and a random pool sufficient to produce structures with high affinity binding to cGMP will be used. The length of the randomized sequences has been chosen to allow sufficient structural complexity to specify the relatively short allosteric bridge structure, which is known to tolerate additions, and a known cGMP binding domain (minimum approximately 32 nucleotides) (Koizumi et al., "Allosteric Ribozymes Sensitive to the Second Messengers cAMP and cGMP," *Nucleic Acids Symp. Ser.* 275-276 (1999); Koizumi et al., "Allosteric Selection of Ribozymes that Respond to the Second Messengers cGMP and cAMP," *Nat. Struct. Biol.* 6:1062-1071 (1999); Breaker, "Engineered Allosteric Ribozymes as Biosensor Components," *Curr. Opin. Biotechnol.* 13:31-39 (2002), which are hereby incorporated by reference in their entirety). As shown in FIG. 11, the cGMP aptamer sequence will be separated by a short stretch of randomized sequences sufficient to optimize the allosteric bridge (Soukup et al., "Engineering Precision RNA Molecular Switches," *Proc. Natl. Acad. Sci. USA* 96:3584-3589 (1999), which is hereby incorporated by reference in its entirety) (N indicates random nucleotide). This strategy will rely on the ability to allosterically link previously optimized structures and assumes only that selection will produce a linkage with sufficient flexibility to retain the individual binding structures, and provide the allosteric interactions. If the structure is too stable, then the length of the random sequence will be altered to adjust stability. The primers will be chosen from Stem 2, minimizing the interference on selection from unrelated primer sequence. This pool will also likely be useful for future selection using other target analytes in addition to cGMP.

Commercially synthesized and annealed dsDNA containing a T7 promoter will be used as the template for in vitro transcription with the T7-MEGA shortscript kit from Ambion. Each aliquot of the RNA pool contains 1-2 copies of 1-2×10$^{15}$ unique RNAs. The selection scheme will contain four steps, as described briefly below:

Step 1: RNA binding to GFP will be performed in 500 µl binding buffer (1×PBS/5 mM MgCl$_2$). The RNA-GFP complex will be partitioned with 0.45 µm nitrocellulose filter or Ni-charged beads (alternating to avoid selection of RNAs binding to either substrate);

Step 2: Elution of RNA from GFP with 100 µM cGMP in PBS;

Step 3: Negative selection will be performed by reacting the eluted mixture with GFP bound to nitrocellulose membrane or Ni-charged beads to eliminate c-GMP independent RNAs in the eluted mixture; and Step 4: Amplify selected RNAs by RT-PCR and RNA for next round synthesized by in vitro transcription using T7-MEGAshortscript. Following 10-15 selection rounds, RNAs will be amplified by RT-PCR, and the DNAs cloned in pGEM-T and sequenced.

Each selected and enriched RNA will be individually examined for its ability to bind to GFP and cGMP, and to GFP in the presence of cGMP. GFP fluorescence in physiological solution will also be examined as a function of RNA concentration in the presence and absence of cGMP. For active (quenching) aptamers, the effect of cGMP on fluorescence will be determined by titration from 10 nM to 10 mM. For RNAs found to be regulated by cGMP, stop-flow fluorescent measurements will be performed to determine the kinetics of the signal under conditions of millisecond rise of cGMP. Fluorescence will be determined in a fluorescence spectrophotometer (FluoroMax 3, Jobin-Yvon, Horiba).

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A nucleic acid aptamer comprising:
a core region comprising the sequence of SEQ ID NO:19;
5' primer region and a 3' primer region; and
one or both of a 5' random nucleotide sequence region and a 3' random nucleotide sequence region, wherein the nucleic acid aptamer has a secondary structure comprising three stems and a central loop and binds to a fluorescent protein selected from GFP, eGFP, eCFP, and eYFP.

2. The nucleic acid aptamer according to claim 1, wherein the nucleic acid aptamer reversibly binds to the fluorescent protein.

3. A molecular complex comprising the nucleic acid aptamer according to claim 1 and a fluorescent protein selected from GFP, eGFP, eCFP, and eYFP bound to the nucleic acid aptamer.

4. The molecular complex according to claim 3, wherein the nucleic acid aptamer is reversibly bound to the fluorescent protein.

5. The molecular complex according to claim 3, wherein the binding of the nucleic acid aptamer alters fluorescence of the fluorescent protein.

6. A host cell containing the molecular complex according to claim 3.

7. A method of detecting a molecular target comprising:
providing the molecular complex according to claim 3 and
contacting the molecular target with the molecular complex under conditions effective to cause a change in fluorescence of the fluorescent protein, whereby the change in fluorescence detects presence of the molecular target.

8. The method according to claim 7, wherein said contacting causes release of the fluorescent protein from the nucleic acid aptamer, an increase in fluorescence, or a decrease in fluorescence, or said contacting inhibits fluorescence.

9. The method according to claim 7, wherein said contacting is carried out in a cell.

10. The method according to claim 9, wherein said providing is carried out by recombinantly expressing the molecular complex in the cell.

11. A method of determining location of a molecular target comprising:

providing the molecular complex according to claim 3;
contacting the molecular target with the molecular complex; and
detecting the fluorescence of the fluorescent protein, whereby location of the molecular target is determined.

12. The method according to claim 11, wherein said contacting is carried out in a cell.

13. The nucleic acid aptamer according to claim 1 comprising both the 5' random nucleotide sequence region and the 3' random nucleotide sequence region.

14. The nucleic acid aptamer according to claim 13, wherein the 5' random nucleotide sequence region, the core region, and the 3' random nucleotide sequence region have nucleotide sequence of SEQ ID NO:22.

15. The nucleic acid aptamer according to claim 13, wherein the 5' random nucleotide sequence region, the core region, and the 3' random nucleotide sequence region have the nucleotide sequence of SEQ ID NO:23.

16. The nucleic acid aptamer according to claim 13, wherein the 5' random nucleotide sequence region, the core region, and the 3' random nucleotide sequence region have the nucleotide sequence of SEQ ID NO:24.

17. The nucleic acid aptamer according to claim 13, wherein the 5' random nucleotide sequence region, the core region, and the 3' random nucleotide sequence region have the nucleotide sequence of SEQ ID NO:25.

18. The nucleic acid aptamer according to claim 13, wherein the 5' random nucleotide sequence region, the core region, and the 3' random nucleotide sequence region have the nucleotide sequence of SEQ ID NO:26.

19. The nucleic acid aptamer according to claim 13, wherein the 5' random nucleotide sequence region, the core region, and the 3' random nucleotide sequence region have the nucleotide sequence of SEQ ID NO:27.

20. The nucleic acid aptamer according to claim 13, wherein the 5' random nucleotide sequence region, the core region, and the 3' random nucleotide sequence region have the nucleotide sequence of SEQ ID NO:28.

21. The nucleic acid aptamer according to claim 1, wherein the aptamer has the nucleotide sequence of SEQ ID NO:29.

* * * * *

SEQUENCE LISTING

```
<160> NUMBER OF SEQ ID NOS: 33

<210> SEQ ID NO 1
<211> LENGTH: 50
<212> TYPE: RNA
<213> ORGANISM: Artificial
<220> FEATURE:
<223> OTHER INFORMATION: aptamer with generic G3 core sequence
<220> FEATURE:
<221> NAME/KEY: misc_feature
<222> LOCATION: (11)..(12)
<223> OTHER INFORMATION: n is a, c, g, or u
<220> FEATURE:
<221> NAME/KEY: misc_feature
<222> LOCATION: (33)..(33)
<223> OTHER INFORMATION: n is a, c, g, or u
<220> FEATURE:
<221> NAME/KEY: misc_feature
<222> LOCATION: (38)..(38)
<223> OTHER INFORMATION: n is a, c, g, or u
<220> FEATURE:
<221> NAME/KEY: misc_feature
<222> LOCATION: (42)..(42)
<223> OTHER INFORMATION: n is a, c, g, or u

<400> SEQUENCE: 1
aucgaauugu nngguagaaa guccuuugag agnaaccngg gnggauacug            50

<210> SEQ ID NO 2
<211> LENGTH: 50
<212> TYPE: RNA
<213> ORGANISM: Artificial
<220> FEATURE:
<223> OTHER INFORMATION: aptamer with specific G3 core sequence

<400> SEQUENCE: 2
aucgaauugu uagguagaaa guccuuugag aggaaccugg gaggauacug            50

<210> SEQ ID NO 3
<211> LENGTH: 50
<212> TYPE: RNA
<213> ORGANISM: Artificial
<220> FEATURE:
<223> OTHER INFORMATION: aptamer with specific G3 core sequence

<400> SEQUENCE: 3
aucgaauugu gugguagaaa guccuuugag agaaaccagg ggggauacug            50

<210> SEQ ID NO 4
<211> LENGTH: 50
<212> TYPE: RNA
<213> ORGANISM: Artificial
<220> FEATURE:
<223> OTHER INFORMATION: aptamer with generic G16 core sequence
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (3)..(3)
<223> OTHER INFORMATION: n is a, c, g, or u
<220> FEATURE:
<221> NAME/KEY: misc_feature
<222> LOCATION: (10)..(10)
<223> OTHER INFORMATION: n is a, c, g, or u
```

```
<220> FEATURE:
<221> NAME/KEY: misc_feature
<222> LOCATION: (25)..(25)
<223> OTHER INFORMATION: n is a, c, g, or u
<220> FEATURE:
<221> NAME/KEY: misc_feature
<222> LOCATION: (39)..(39)
<223> OTHER INFORMATION: n is a, c, g, or u

<400> SEQUENCE: 4
ngngaauugn guggggaaag uccunaaaag agggccacng ccgaaacgcc            50

<210> SEQ ID NO 5
<211> LENGTH: 50
<212> TYPE: RNA
<213> ORGANISM: Artificial
<220> FEATURE:
<223> OTHER INFORMATION: aptamer with sepcific G16 core sequence

<400> SEQUENCE: 5
ugugaauugg guggggaaag uccugaaaag agggccaccg ccgaaacgcc            50

<210> SEQ ID NO 6
<211> LENGTH: 50
<212> TYPE: RNA
<213> ORGANISM: Artificial
<220> FEATURE:
<223> OTHER INFORMATION: aptamer with specific G16 core sequence

<400> SEQUENCE: 6
ugcgaauugg guggggaaag uccugaaaag agggccaccg ccgaaacgcc            50

<210> SEQ ID NO 7
<211> LENGTH: 50
<212> TYPE: RNA
<213> ORGANISM: Artificial
<220> FEATURE:
<223> OTHER INFORMATION: aptamer with specific G16 core sequence

<400> SEQUENCE: 7
ugugaauuga guggggaaag uccugaaaag agggccacug ccgaaacgcc            50

<210> SEQ ID NO 8
<211> LENGTH: 50
<212> TYPE: RNA
<213> ORGANISM: Artificial
<220> FEATURE:
<223> OTHER INFORMATION: aptamer with specific G16 core sequence

<400> SEQUENCE: 8
ugugaauugg guggggaaag uccuaaaaag agggccaccg ccgaaacgcc            50

<210> SEQ ID NO 9
<211> LENGTH: 50
<212> TYPE: RNA
<213> ORGANISM: Artificial
<220> FEATURE:
<223> OTHER INFORMATION: aptamer with specific G16 core sequence

<400> SEQUENCE: 9
ggugaauugg guggggaaag uccuaaaaag agggccaccg ccgaaacgcc            50

<210> SEQ ID NO 10
<211> LENGTH: 50
<212> TYPE: RNA
<213> ORGANISM: Artificial
<220> FEATURE:
<223> OTHER INFORMATION: aptamer with specific G16 core sequence
```

-continued

<400> SEQUENCE: 10
ugugaauuga gugggaaag uccugaaaag agggccaccg ccgaaacgcc    50

<210> SEQ ID NO 11
<211> LENGTH: 50
<212> TYPE: RNA
<213> ORGANISM: Artificial
<220> FEATURE:
<223> OTHER INFORMATION: aptamer with specific G16 core sequence

<400> SEQUENCE: 11
ugugaauuga gugggaaag uccugaaaag agggccacag ccgaaacgcc    50

<210> SEQ ID NO 12
<211> LENGTH: 50
<212> TYPE: RNA
<213> ORGANISM: Artificial
<220> FEATURE:
<223> OTHER INFORMATION: aptamer with G10 core

<400> SEQUENCE: 12
guuggauugu uaggauaaag cccguaaagg agggccuua agagcuccag    50

<210> SEQ ID NO 13
<211> LENGTH: 50
<212> TYPE: RNA
<213> ORGANISM: Artificial
<220> FEATURE:
<223> OTHER INFORMATION: aptamer with core derived from G3, G16, G20

<400> SEQUENCE: 13 uuggggugg gugggaaag uccuuaaaag agggccacca cagaagcaau    50

<210> SEQ ID NO 14
<211> LENGTH: 51
<212> TYPE: RNA
<213> ORGANISM: Artificial
<220> FEATURE:
<223> OTHER INFORMATION: aptamer with No Quench 1 core

<400> SEQUENCE: 14
uucgaccgag cgaggccuag aaccgaguac caacauaaaa aaaaaaccg a    51

<210> SEQ ID NO 15
<211> LENGTH: 50
<212> TYPE: RNA
<213> ORGANISM: Artificial
<220> FEATURE:
<223> OTHER INFORMATION: aptamer with No Quench 2 core

<400> SEQUENCE: 15
cgcaaauaau aagaacaaca aagauggccu agacaaaaac ccggagcgau    50

<210> SEQ ID NO 16
<211> LENGTH: 50
<212> TYPE: RNA
<213> ORGANISM: Artificial
<220> FEATURE:
<223> OTHER INFORMATION: aptamer with No Quench 3 core

<400> SEQUENCE: 16
cuugaaaaaa cuccugaaac cgaggcagaa uuaaaaacaa uuacaacaga    50

<210> SEQ ID NO 17
<211> LENGTH: 50

```
<212> TYPE: RNA
<213> ORGANISM: Artificial
<220> FEATURE:
<223> OTHER INFORMATION: aptamer with No Quench 4 core

<400> SEQUENCE: 17
cgugcaauga cacgcagcgu caagacugag ugauucgacc aacgaccgca               50

<210> SEQ ID NO 18
<211> LENGTH: 50
<212> TYPE: RNA
<213> ORGANISM: Artificial
<220> FEATURE:
<223> OTHER INFORMATION: aptamer with No Quench 5 core

<400> SEQUENCE: 18
gccagugagc cgauggaacc gaggcgacuu aaagaaaaac acaacagagc               50

<210> SEQ ID NO 19
<211> LENGTH: 36
<212> TYPE: RNA
<213> ORGANISM: Artificial
<220> FEATURE:
<223> OTHER INFORMATION: aptamer
<220> FEATURE:
<221> NAME/KEY: misc_feature
<222> LOCATION: (13)..(13)
<223> OTHER INFORMATION: N at position 13 is optional and can be G

<400> SEQUENCE: 19
gaauugdkwg gknaaagucc udaaaagagg gccacc                              36

<210> SEQ ID NO 20
<211> LENGTH: 16
<212> TYPE: RNA
<213> ORGANISM: Artificial
<220> FEATURE:
<223> OTHER INFORMATION: 5' primer

<400> SEQUENCE: 20
gggagcacga uuccau                                                    16

<210> SEQ ID NO 21
<211> LENGTH: 20
<212> TYPE: RNA
<213> ORGANISM: Artificial
<220> FEATURE:
<223> OTHER INFORMATION: 3' primer

<400> SEQUENCE: 21
uacaagcuuc uggacucggu                                                20

<210> SEQ ID NO 22
<211> LENGTH: 101
<212> TYPE: RNA
<213> ORGANISM: Artificial
<220> FEATURE:
<223> OTHER INFORMATION: aptamer AP2

<400> SEQUENCE: 22
gcaauugucg aguguuagc agcagcuugc auauugaguc guggcgaauu ggguggggaa     60
aguccuaaaa agagggccac cacagagguu uguacccaua c                       101

<210> SEQ ID NO 23
<211> LENGTH: 107
<212> TYPE: RNA
<213> ORGANISM: Artificial
```

```
<220> FEATURE:
<223> OTHER INFORMATION: aptamer AP3

<400> SEQUENCE: 23
gcgugagacg ucuugaugaa auccggcucg gcaaugguuc guggcgaauu ggguggggaa      60
aguccuuaaa agagggccac cacagaagcu guggaguua acagcaa                  107

<210> SEQ ID NO 24
<211> LENGTH: 121
<212> TYPE: RNA
<213> ORGANISM: Artificial
<220> FEATURE:
<223> OTHER INFORMATION: aptamer AP4

<400> SEQUENCE: 24
gauucucgua ucaaggaagg guuaugagau uuagguaaac guggcgaauu ggguggggaa      60
aguccuaaaa agagggccac cacagaggcu guaaucgau guuacuauag agggacacga    120
c                                                                   121

<210> SEQ ID NO 25
<211> LENGTH: 121
<212> TYPE: RNA
<213> ORGANISM: Artificial
<220> FEATURE:
<223> OTHER INFORMATION: aptamer AP5

<400> SEQUENCE: 25
guagcgugug gaucaucacc uaugacccgg cuacgguuuc guggcgaauu ggguggggaa      60
aguccuraaa agagggccac cacagaagcc auuucgaaua cucguccuug cacaguaucg    120
a                                                                   121

<210> SEQ ID NO 26
<211> LENGTH: 121
<212> TYPE: RNA
<213> ORGANISM: Artificial
<220> FEATURE:
<223> OTHER INFORMATION: aptamer AP6

<400> SEQUENCE: 26
uggaugccac cgcgacuacg guuaguaggc auucugaguc guggcgaauu ggguggggaa      60
aguccugaaa agagggccac cacagaggcu caaacuggac guuaaugacg uuucgguuca    120
g                                                                   121

<210> SEQ ID NO 27
<211> LENGTH: 121
<212> TYPE: RNA
<213> ORGANISM: Artificial
<220> FEATURE:
<223> OTHER INFORMATION: aptamer AP7

<400> SEQUENCE: 27
acggaaagag guaauuaugc aucuccaaug uguaugguuc guggcgaauu ggguggggaa      60
aguccugaaa agagggccac cacggaagcu uaacggagag gagcuggggc gccuuuuccg    120
a                                                                   121

<210> SEQ ID NO 28
<211> LENGTH: 121
<212> TYPE: RNA
<213> ORGANISM: Artificial
<220> FEATURE:
<223> OTHER INFORMATION: aptamer AP8
```

```
<400> SEQUENCE: 28
uuuuaauucg ccgugacacg ucgcggucaa gaauggcuuc guggcgaauu ggguggggaa    60
aguccugaaa agagggccac cacagaagcg cugcuugacc aucaauccga aucgucaagu   120
g                                                                   121

<210> SEQ ID NO 29
<211> LENGTH: 83
<212> TYPE: RNA
<213> ORGANISM: Artificial
<220> FEATURE:
<223> OTHER INFORMATION: aptamer with minimal core sequence

<400> SEQUENCE: 29
gggagcacga uggcguggcg aauugggugg ggaaaguccu uaaaagaggg ccaccacaga    60
agcaaugggc uucuggacuc ggu                                           83

<210> SEQ ID NO 30
<211> LENGTH: 83
<212> TYPE: RNA
<213> ORGANISM: Artificial Sequence
<220> FEATURE:
<223> OTHER INFORMATION: GFP aptamer

<400> SEQUENCE: 30
gggagccuga uggcagggcg aauugggugg ggaaaguccu uaaaagacgg ccaccacaga    60
agcaacgggc uucuggacuc ggu                                           83

<210> SEQ ID NO 31
<211> LENGTH: 121
<212> TYPE: RNA
<213> ORGANISM: Artificial Sequence
<220> FEATURE:
<223> OTHER INFORMATION: aptamer
<220> FEATURE:
<221> NAME/KEY: misc_feature
<222> LOCATION: (16)..(60)
<223> OTHER INFORMATION: n at positions 16 to 60 is a, c, g, or u

<400> SEQUENCE: 31
gggcuucugg acucgnnnnn nnnnnnnnnn nnnnnnnnnn nnnnnnnnnn nnnnnnnnnn    60
ccugauggca gggcgaauug gcuggggaaa guccucaaaa gaggcccacc acagaagcaa   120
u                                                                   121

<210> SEQ ID NO 32
<211> LENGTH: 123
<212> TYPE: RNA
<213> ORGANISM: Artificial Sequence
<220> FEATURE:
<223> OTHER INFORMATION: aptamer
<220> FEATURE:
<221> NAME/KEY: misc_feature
<222> LOCATION: (18)..(21)
<223> OTHER INFORMATION: n at positions 18 to 21 is a, c, g, or u
<220> FEATURE:
<221> NAME/KEY: misc_feature
<222> LOCATION: (54)..(57)
<223> OTHER INFORMATION: n at positions 54 to 57 is a, c, g, or u

<400> SEQUENCE: 32
gggcuucugg acucggunnn nccuugcgau gcaaaaaggu gcugacgaca cgunnnnggg    60
agccugaugc cagcgcgaau uggguggggg aagucgguaa aagagggcca ccacagaagc   120
aau                                                                 123
```

```
<210> SEQ ID NO 33
<211> LENGTH: 157
<212> TYPE: RNA
<213> ORGANISM: Artificial Sequence
<220> FEATURE:
<223> OTHER INFORMATION: aptamer
<220> FEATURE:
<221> NAME/KEY: misc_feature
<222> LOCATION: (17)..(61)
<223> OTHER INFORMATION: N at position 17 to 61 is a, c, g, or u
<220> FEATURE:
<221> NAME/KEY: misc_feature
<222> LOCATION: (97)..(137)
<223> OTHER INFORMATION: N at position 97 to 137 is a, c, g, or u

<400> SEQUENCE: 33
gggagcacga uuccaunnnn nnnnnnnnnn nnnnnnnnnn nnnnnnnnnn nnnnnnnnnn     60
ngaauugggu gggaaaaguc cugaaaagag ggccaccnnn nnnnnnnnnn nnnnnnnnnn    120
nnnnnnnnnn nnnnnnnuac aagcuucugg acucggu                             157
```